United States Patent
Kralles et al.

(10) Patent No.: US 8,672,543 B2
(45) Date of Patent: Mar. 18, 2014

(54) COUNTERWEIGHT FOR MOBILE X-RAY DEVICE

(75) Inventors: Christopher J. Kralles, Rochester, NY (US); Anthony DiRisio, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 236 days.

(21) Appl. No.: 13/083,751

(22) Filed: Apr. 11, 2011

(65) Prior Publication Data

US 2011/0249805 A1     Oct. 13, 2011

Related U.S. Application Data

(60) Provisional application No. 61/323,503, filed on Apr. 13, 2010, provisional application No. 61/323,497, filed on Apr. 13, 2010, provisional application No. 61/323,499, filed on Apr. 13, 2010.

(51) Int. Cl.
*H05G 1/02*     (2006.01)

(52) U.S. Cl.
USPC ............................. 378/198; 378/102; 378/197

(58) Field of Classification Search
USPC .................. 378/102, 198, 197, 193, 194, 196
See application file for complete search history.

(56) References Cited

U.S. PATENT DOCUMENTS

| | | | |
|---|---|---|---|
| 2,041,242 A | 5/1936 | Goldfield | |
| 4,341,279 A | 7/1982 | Waerve | |
| 4,716,581 A | 12/1987 | Barud | |
| 5,067,145 A | 11/1991 | Siczek et al. | |
| 5,425,069 A * | 6/1995 | Pellegrino et al. | 378/198 |
| 5,475,730 A | 12/1995 | Galando | |
| 5,499,284 A | 3/1996 | Pellegrino et al. | |
| 5,844,961 A | 12/1998 | McEvoy et al. | |
| 6,193,415 B1 * | 2/2001 | Kadowaki et al. | 378/198 |
| 6,491,430 B1 | 12/2002 | Scissler | |
| 6,851,853 B2 | 2/2005 | Nakagawa et al. | |
| 7,016,467 B2 | 3/2006 | Brooks | |
| 7,211,802 B1 | 5/2007 | Dhurjaty et al. | |
| 7,495,226 B2 | 2/2009 | Jadrich et al. | |
| 7,611,282 B2 | 11/2009 | Koren et al. | |
| 2003/0190014 A1 | 10/2003 | Nakagawa et al. | |

FOREIGN PATENT DOCUMENTS

WO     90-14748     11/1990

OTHER PUBLICATIONS

International Search Report & Written Opinion, International application No. PCT/US2011/032041, dated Dec. 12, 2011, 9 pages.

* cited by examiner

*Primary Examiner* — Hoon Song

(57) ABSTRACT

A mobile radiography apparatus has a portable transport frame. A sectioned vertical column mounted on the frame defines a vertical axis and has a base section having a fixed vertical position relative to the vertical axis and at least one movable section that is translatable to a variable vertical position. A boom apparatus supports an x-ray source and extends outward from the movable section and has an adjustable height relative to the vertical axis. A counterweight is operatively coupled to the boom apparatus to support displacement of the boom apparatus to any of a plurality of vertical positions along the movable section, wherein the counterweight, in cooperation with boom apparatus movement, travels along a shaft that extends within the movable section, wherein, at one or more of the height positions of the boom apparatus, a portion of the counterweight extends upward above the shaft of the sectioned vertical column.

20 Claims, 42 Drawing Sheets

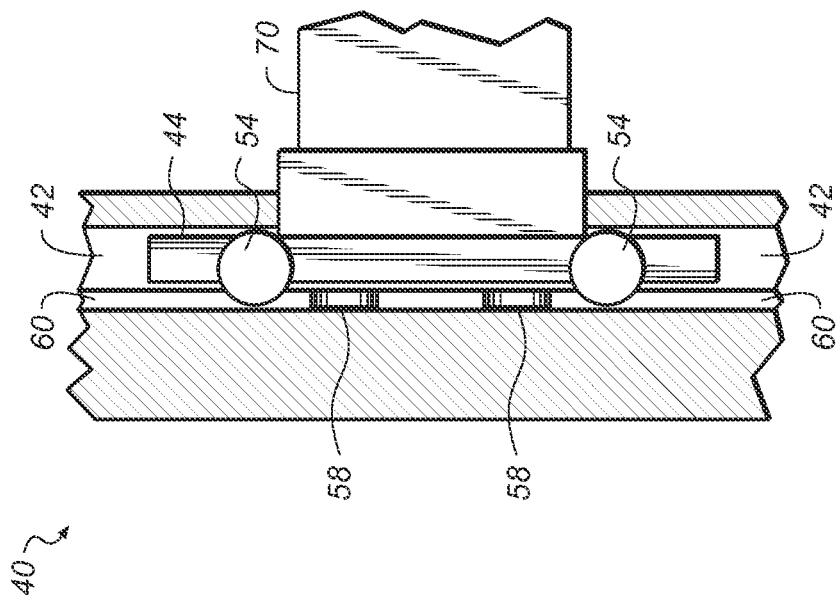
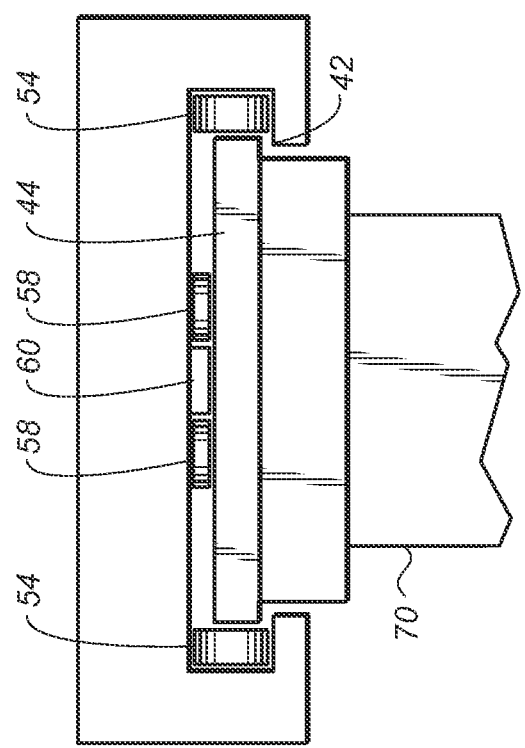
FIG. 24A
FIG. 24B

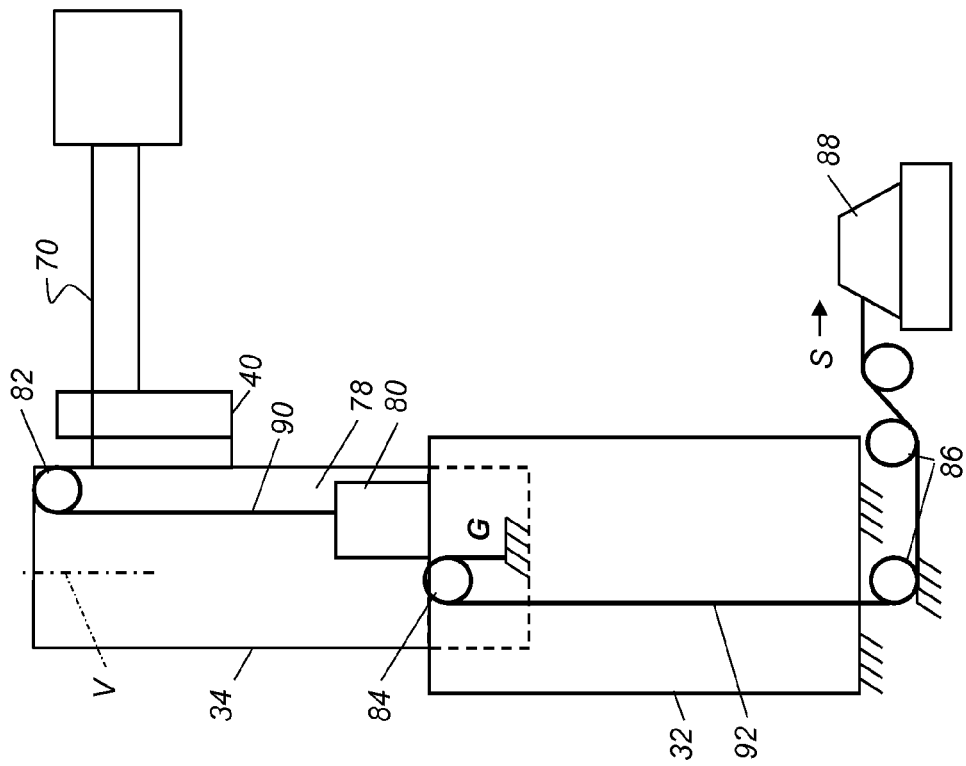
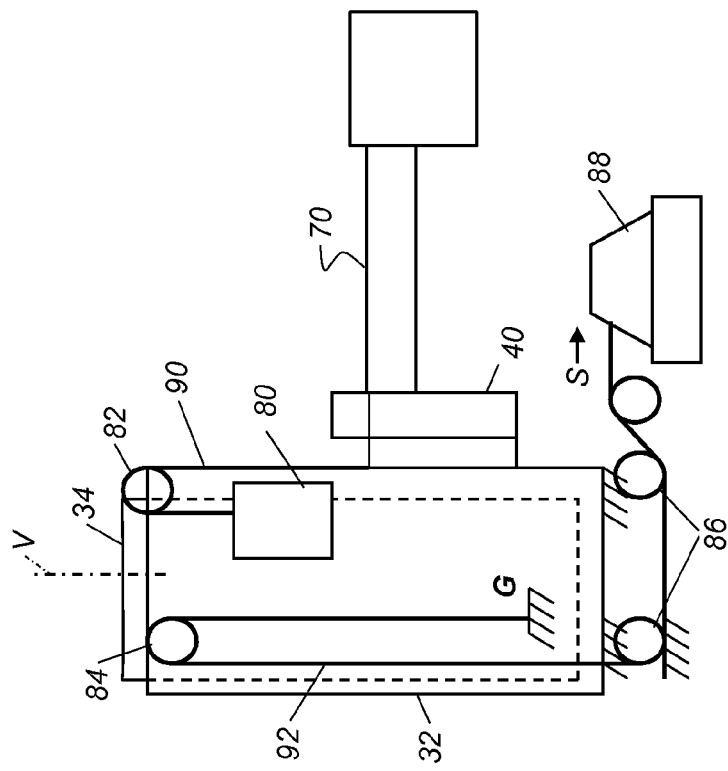

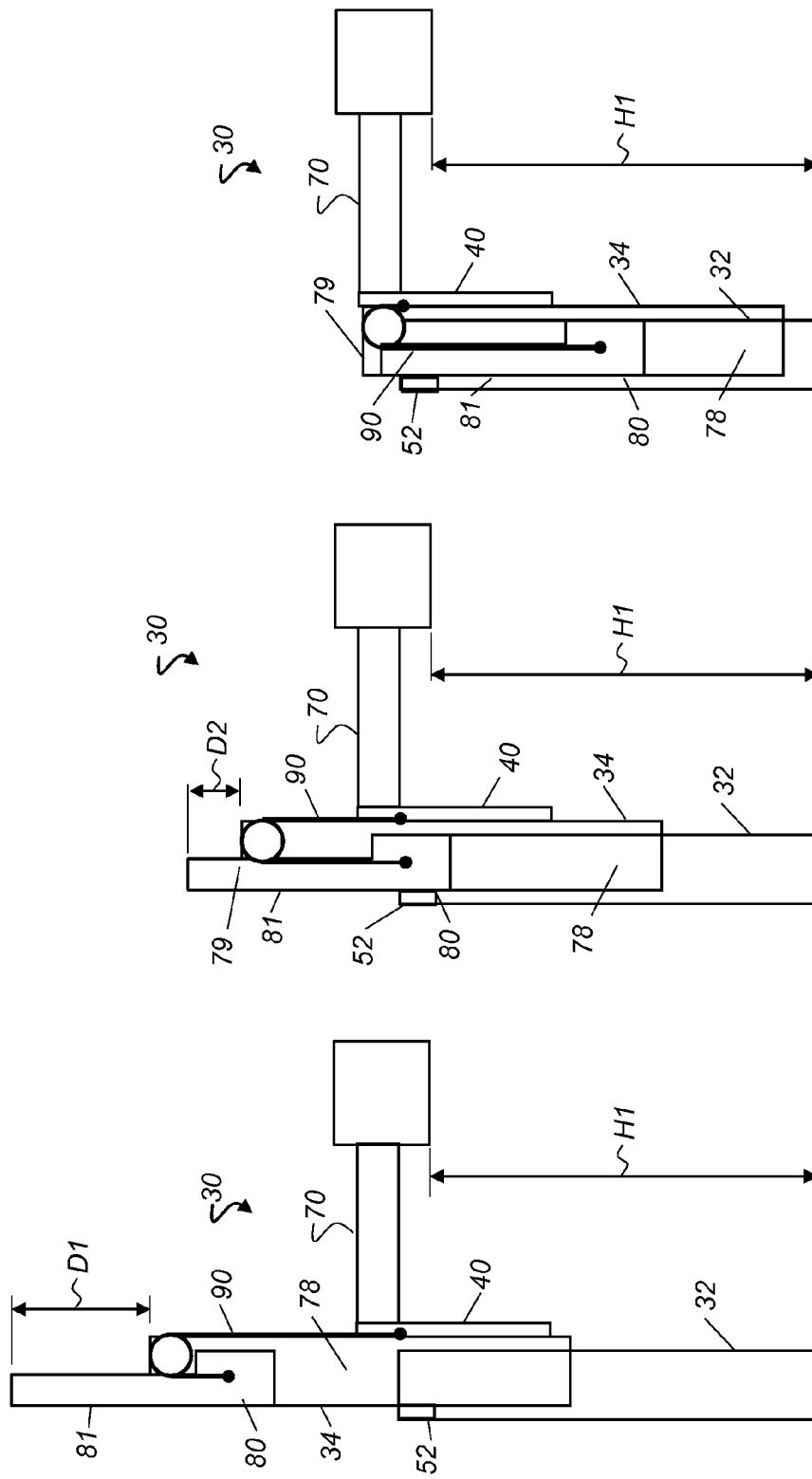

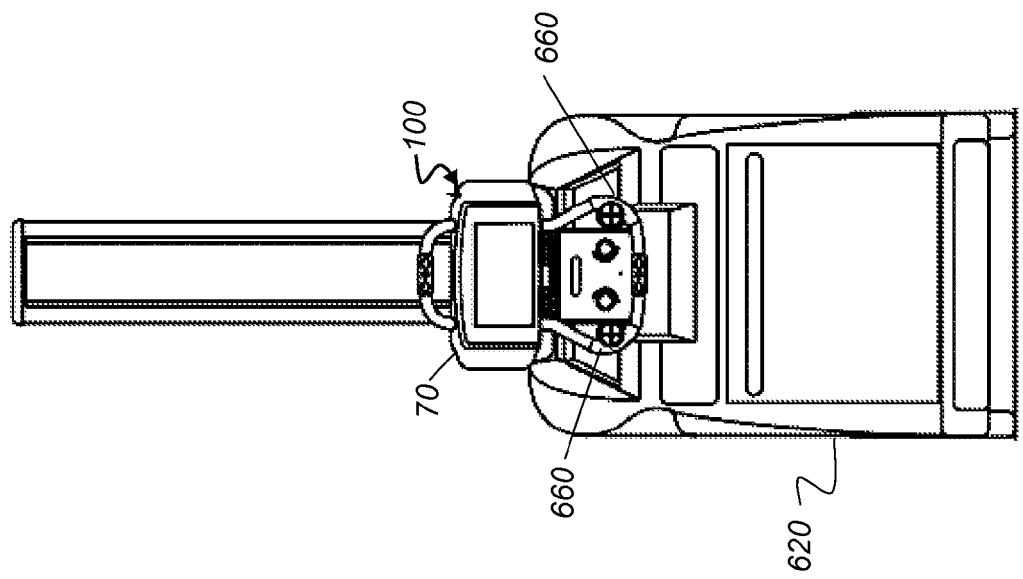

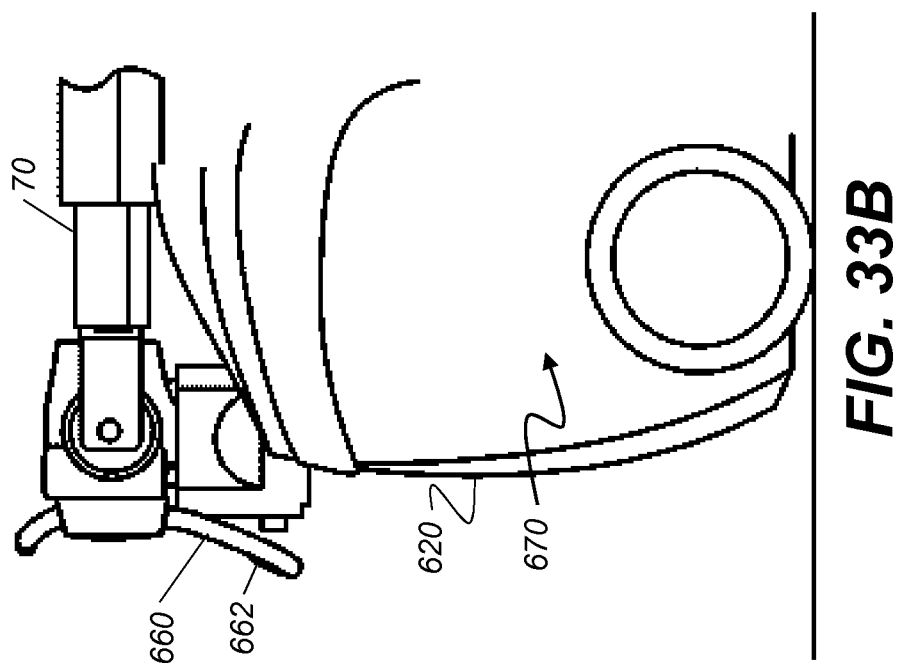

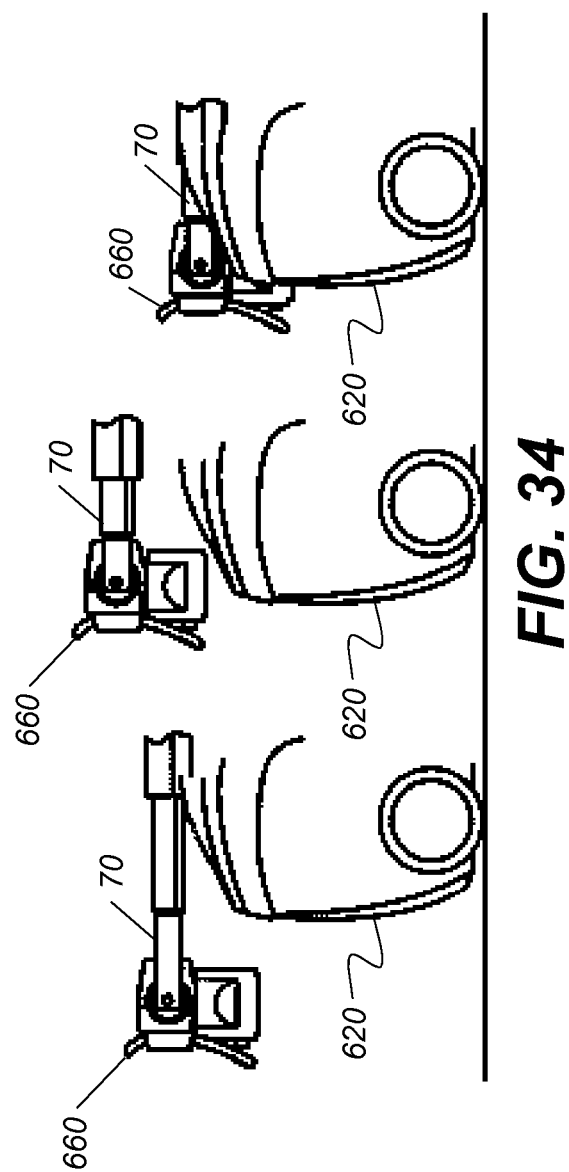

COUNTERWEIGHT FOR MOBILE X-RAY DEVICE

CROSS REFERENCE TO RELATED APPLICATIONS

Reference is made to, and priority is claimed from, U.S. Ser. No. 61/323,503, filed as a provisional patent application on Apr. 13, 2010, entitled "MOBILE UNIT HAVING COLLAPSIBLE COLUMN", in the names of James H. Ogle, Jr. et al. and commonly assigned; from U.S. Ser. No. 61/323,497, also filed as a provisional patent application on Apr. 13, 2010, entitled "MOBILE UNIT HAVING ADJUSTABLE DRIVE HANDLE", in the names of Christopher J. Kralles, et al. and commonly assigned; and from U.S. Ser. No. 61/323,499, also filed as a provisional patent application on Apr. 13, 2010, entitled "MOBILE UNIT HAVING DRIVE HANDLE", in the names of Christopher J. Kralles, et al. and commonly assigned.

FIELD OF THE INVENTION

The present invention relates generally to the field of radiography and in particular to portable radiographic imaging apparatus. More specifically, the invention relates to a mobile radiography apparatus having a support column with a counterweight for adjusting the height of radiography components.

BACKGROUND OF THE INVENTION

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 that allows functions such as storing, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a support member 635 that supports an x-ray source 640, also termed an x-ray tube, tube head, or generator mounted on a boom apparatus 70, more simply termed a boom 70. In the embodiment shown, support member 635 has a vertical column 64 of fixed height. Boom 70 extends outward a variable distance from support member 635 and rides up and down column 64 to the desired height for obtaining the image. Boom 70 may extend outward by a fixed distance or may be extendible over a variable distance. Height settings for the x-ray source 640 can range from low height, for imaging feet and lower extremities, to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

One concern that must be addressed in design of the support member relates to ease of positioning of the x-ray source mounted on its boom. For ease of operation under varying conditions, the technician should be able to easily position and orient the x-ray source without requiring both hands, without the need of additional tools, and without needing help from nearby personnel. This includes moving the x-ray source from its docked position used in transport to an imaging position. The mechanical problem of providing ease of positioning is complicated by the weight of the x-ray source and by its extension outward from the vertical axis, While the conventional mobile x-ray apparatus described as unit 600 provides portable imaging capability in a number of applications, however, there are drawbacks to existing designs that can make these devices difficult to deploy in some circumstances. One of the problems common to conventional designs is due, in part, to the relative mobility and range of motion of the mobile x-ray apparatus that is needed.

The side view of FIG. 2 shows a significant problem that occurs when transporting a mobile radiography system, shown as a mobile radiography unit 62 that uses a fixed vertical structure, column 64. Boom 70 that provides transport of x-ray source 68, normally extended outward from unit 62 when in its imaging position, is folded back toward a technician 66 for transport. This transport position helps to protect the x-ray source from damage or from causing an obstruction during movement. Column 64, however, obstructs the view of technician 66 when moving the unit from one place to another, so that objects that are near the front edge of unit 62 or directly in front of the unit cannot readily be seen. The technician is required to peer around the column during transport and can be more prone to colliding or bumping against other equipment or obstacles in the hospital ward or other location. The fixed vertical column 64 may also present difficulties when passing or moving alongside accessory equipment, furniture, or patient support equipment. With obstructed vision, the technician must move slowly, impacting productivity and response time. Accidents and mishaps are more likely.

One type of solution for alleviating the problem described with reference to FIG. 2 is to provide a collapsible column 64, as described in commonly assigned U.S. Patent Application Ser. No. 61/323,503 filed Apr. 13, 2010 in the names of Wendlandt et al. Whether column 64 is fixed or collapsible, however, the mechanical challenge of making boom 70 easy to manipulate without requiring considerable lifting effort remains.

Thus, there is a need for improvements in mobile x-ray apparatus design that allow ease of movement of the boom transport mechanism.

SUMMARY OF THE INVENTION

An object of the present invention is to advance the art of mobile radiography. Another object of the present invention is to address the need for a mobile radiography unit that allows ease of movement of the boom assembly between vertical positions.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

From one aspect, the present invention can provide a mobile radiography apparatus comprising a portable transport frame; a sectioned vertical column mounted on the frame and defining a vertical axis and comprising a base section having a fixed vertical position relative to the vertical axis and at least one movable section that is translatable to a variable vertical position along the vertical axis; a boom apparatus that supports an x-ray source and extends outward from the movable section and has an adjustable height relative to the vertical axis for positioning the x-ray source; and a counterweight that is operatively coupled to the boom apparatus to support displacement of the boom apparatus to any of a plurality of vertical positions along the movable section, wherein the counterweight, in cooperation with boom apparatus movement, travels along a shaft that extends within the movable section of the vertical column; wherein, at one or more of the height positions of the boom apparatus, a portion of the counterweight extends upward above the shaft of the sectioned vertical column.

From another aspect, the present invention can provide a mobile radiography apparatus comprising a portable transport frame; a sectioned vertical column mounted on the frame and defining a vertical axis and comprising a base section having a fixed vertical position relative to the vertical axis and at least a first movable section that is translatable to a variable vertical position along the vertical axis; a boom transport mechanism on the first movable section, wherein the boom transport mechanism is actuable to adjust to a height position by moving along at least a portion of the first movable section; a boom apparatus that supports an x-ray source and is coupled to the boom transport mechanism and extends outward with respect to the sectioned vertical column; and a counterweight that is operatively coupled to the boom transport mechanism for displacement to any of a plurality of vertical positions, along a shaft that extends within the first movable section of the vertical column, in cooperation with boom apparatus movement, wherein the counterweight has a vertical cavity that is disposed to accept a cable that travels inside the counterweight, the cable extending between two or more pulleys that provide movement of the first movable section.

From another aspect, the present invention can provide a method for mounting an x-ray source for use at variable heights, the method comprising providing a sectioned vertical column that comprises a base section having a fixed vertical position relative to a vertical axis and at least a first movable section that is translatable to a variable vertical position along the vertical axis; coupling a boom transport mechanism onto the first movable section, wherein the boom transport mechanism is actuable to provide vertical movement along at least a portion of the first movable section; coupling a boom apparatus to the boom transport mechanism, the boom transport mechanism having an x-ray source for positioning at a desired height; and coupling a counterweight to the boom transport mechanism, wherein the counterweight travels in the direction of the vertical axis within a shaft in the first movable section of the vertical column and wherein a portion of the counterweight extends upward above the shaft at one or more positions of the boom transport mechanism.

From another aspect, the present invention can provide a mobile radiography apparatus comprising a wheeled transport frame; a boom coupled to the transport frame and supporting an x-ray source; and a transport drive system comprising a drive handle responsive to operator control for movement and steering, wherein the drive handle is adjustable for at least one of height and extension.

From another aspect, the present invention can provide a mobile radiography apparatus comprising a wheeled transport frame; a boom coupled to the transport frame and supporting an x-ray source; and a transport drive system comprising a drive handle that is mounted on the boom and that is responsive to operator control for movement and steering.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 24A is a top view showing the carriage mechanism of the boom transport in one embodiment.

FIG. 24B is a side view showing the carriage mechanism of the boom transport in the FIG. 24A embodiment.

FIGS. 25A and 25B show schematically how a counterweight is deployed in order to provide a lifting force for a boom apparatus in an embodiment of the present invention that uses a sectioned vertical column.

FIGS. 27A, 27B, and 27C are schematic views that show a number of possible combinations for achieving the same height for the boom apparatus using an embodiment with an elongated counterweight.

FIG. 33A is a front view of the portable radiography apparatus with its boom apparatus in a docked position.

FIG. 33B is a side view of the portable radiography apparatus with its boom apparatus in a docked position.

FIG. 34 shows side views of the portable radiography apparatus with its boom apparatus in a docked position and handles at different heights.

DETAILED DESCRIPTION OF THE INVENTION

Figure 1:
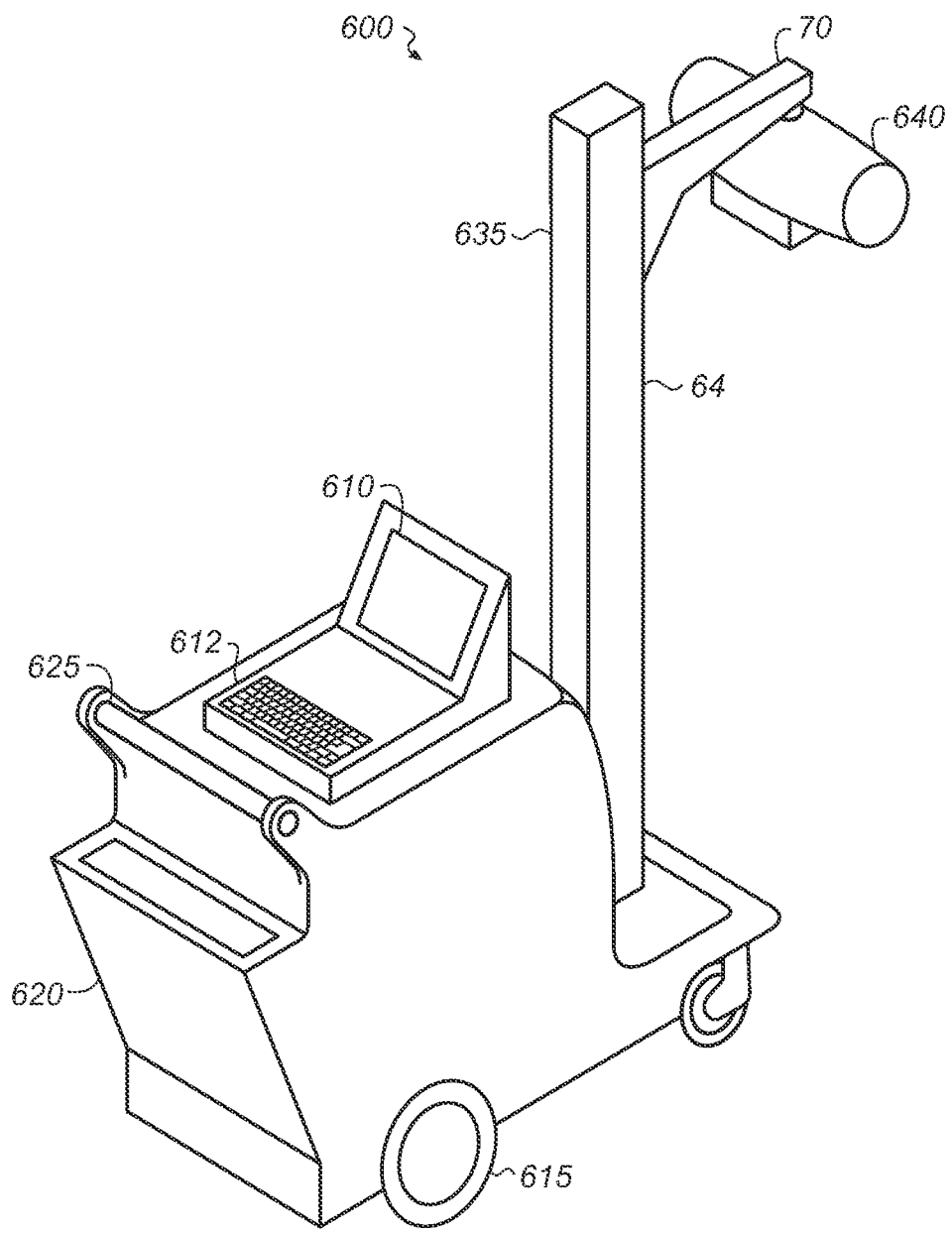
FIG. 1 shows a perspective view of a conventional mobile radiography unit using a fixed length vertical column for positioning the x-ray source.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal or priority relation, but may be used for more clearly distinguishing one element or time interval from another.

Figure 2:
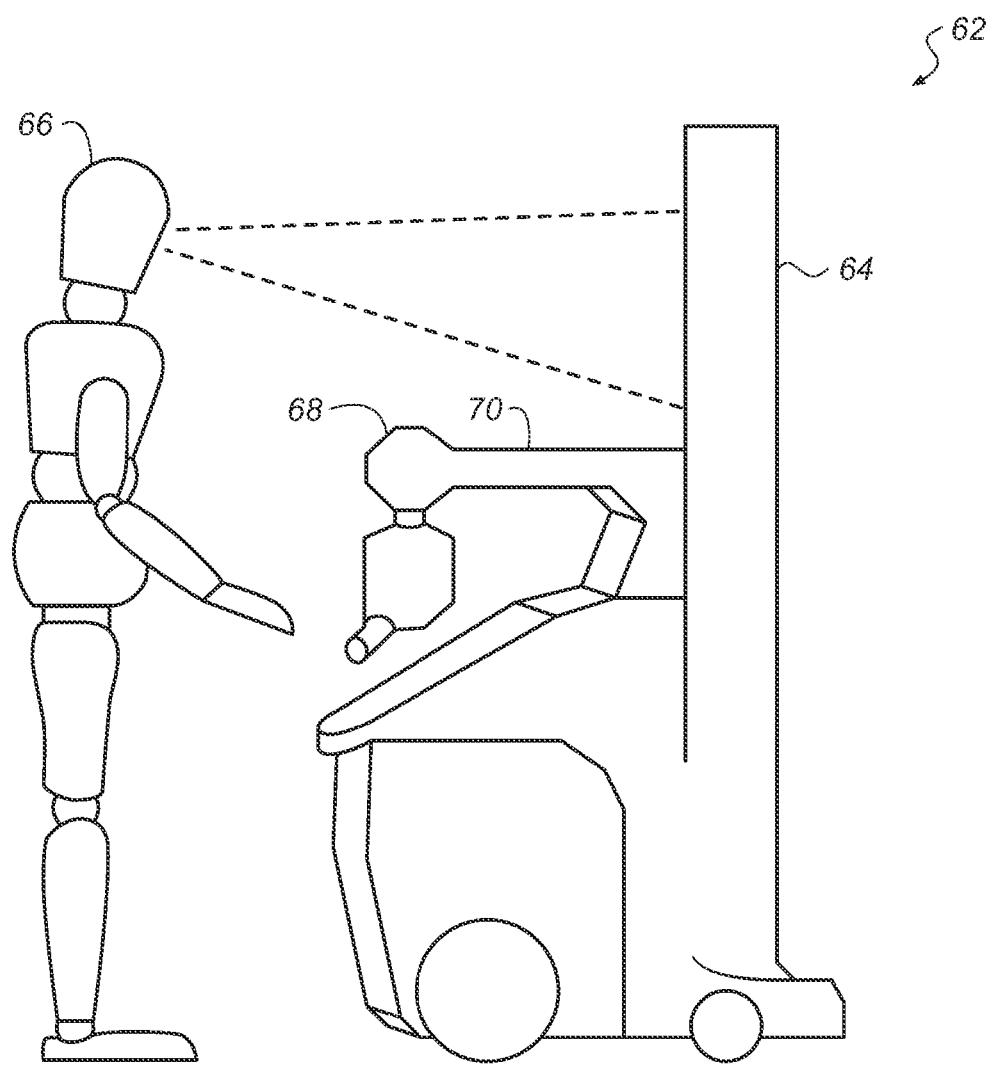
FIG. 2 shows a side view of a conventional mobile radiography unit with a fixed vertical column for positioning the x-ray source.

Apparatus and methods of the present invention address the need for a radiography unit that can be readily wheeled from one place to another within a treatment facility, without the physical or visual obstruction that is common to many types of conventional mobile radiography equipment that use a vertical column. As noted previously, the x-ray source of such a system must allow elevation over a wide vertical range of motion, from heights near or above shoulder level for adults to very low elevations near the ankle or foot. One way to achieve this range of movement is the use of a jointed support member, as described previously. A somewhat simpler mechanical design is the use of a stationary vertical column as was shown in FIGS. 1 and 2, with the x-ray source mounted on a boom that extends outward horizontally from the column and travels vertically up and down the column. Two degrees of freedom are needed for boom 70 relative to the vertical column: translation along the vertical direction, that is, along the vertical axis, and rotation about the vertical axis. Boom 70 typically also extends to a variable horizontal length in a direction relative to the vertical axis, although it should be noted that a boom of fixed length could be used in a mobile radiography apparatus of the present invention.

Figure 3:
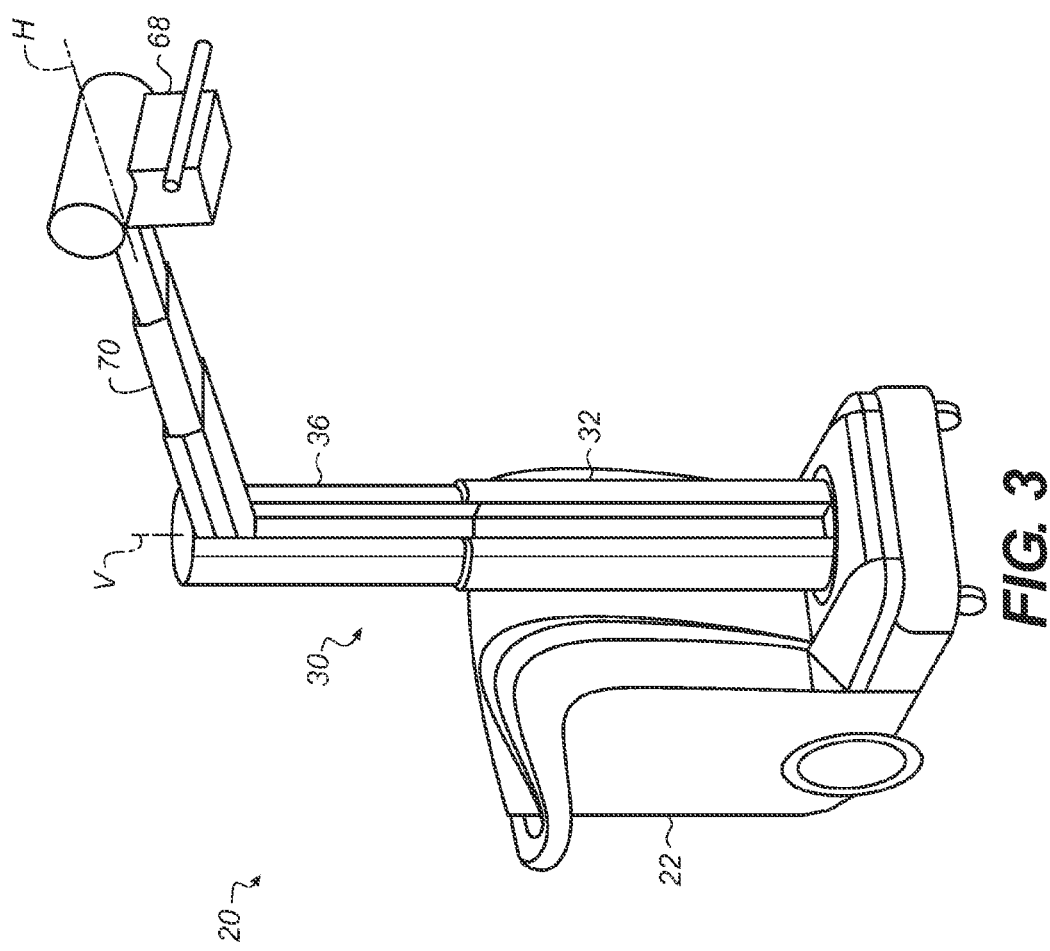
FIG. 3 shows a perspective view of a mobile radiography unit with a sectioned vertical column according to one embodiment of the present invention.
Figure 4:
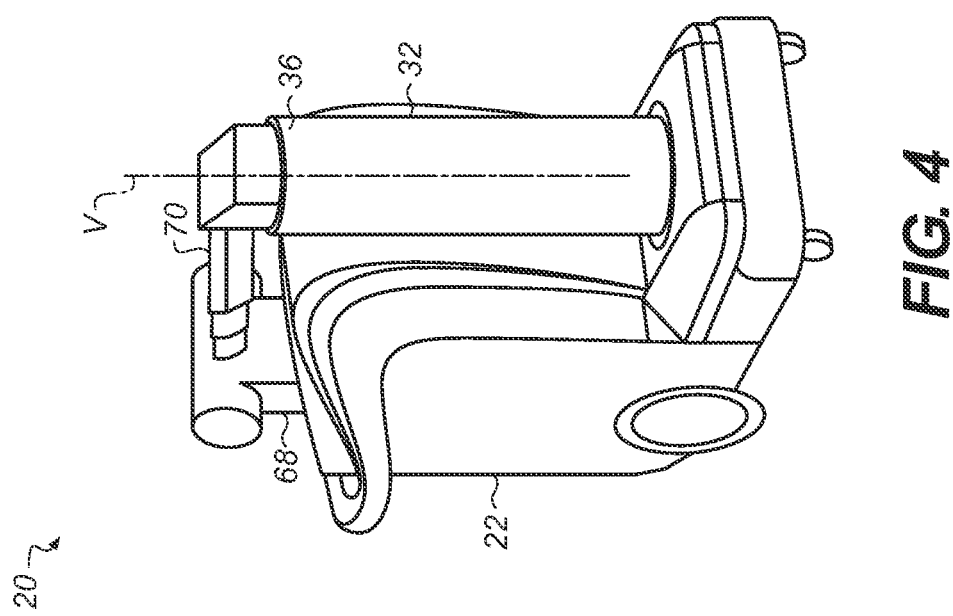
FIG. 4 shows a perspective view of a mobile radiography unit with a sectioned vertical column configured for travel.
Figure 5:
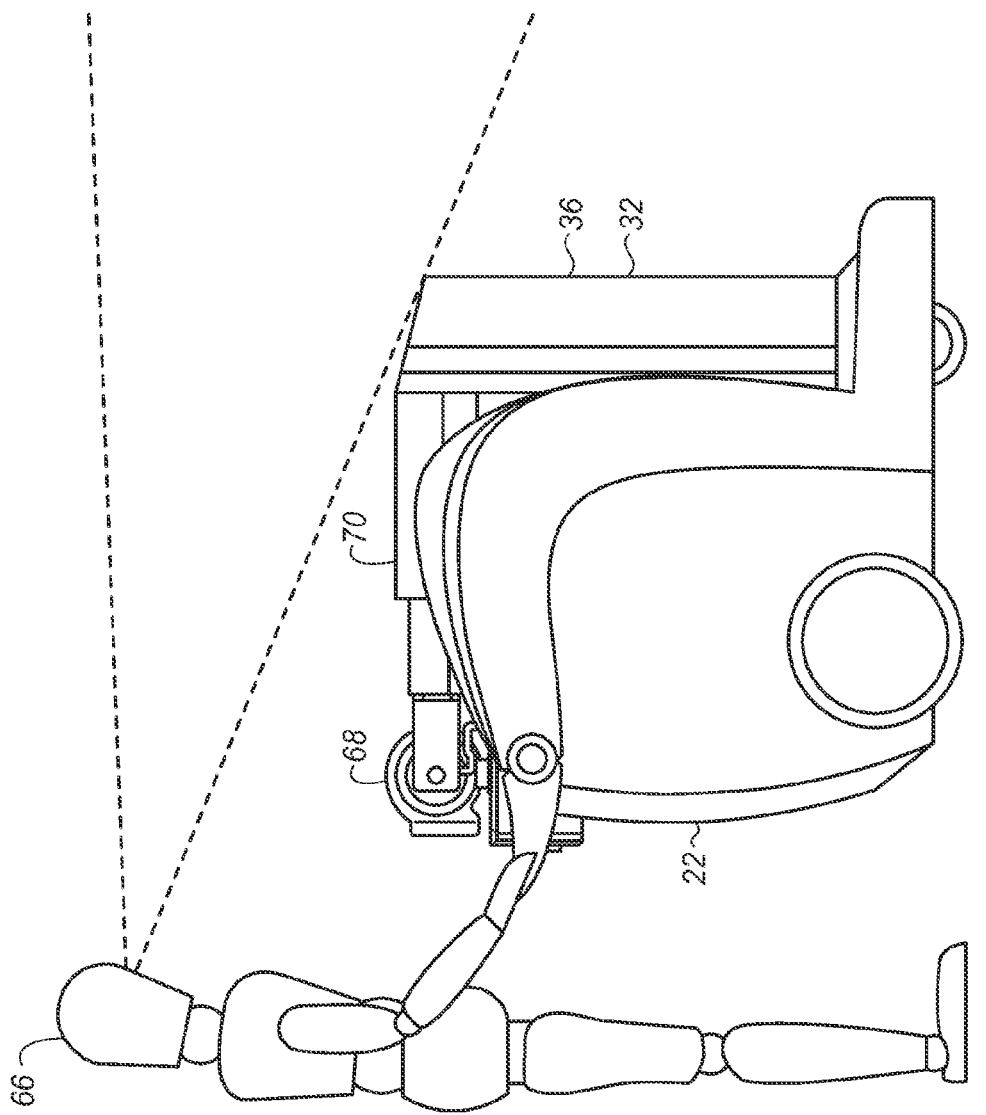
FIG. 5 shows a side view of a mobile radiography unit with a sectioned vertical column according to one embodiment of the present invention.

The perspective view of FIG. 3 shows a mobile radiography unit 20 that has boom 70 coupled to a sectioned vertical column 30 according to one embodiment. FIG. 3 shows unit 20 with x-ray source 68 in position for imaging, extended outward and supported on boom 70, along a horizontal axis H that is perpendicular to the vertical axis V. FIG. 4 shows unit 20 in an alternate, docked arrangement, configured for travel, with sectioned vertical column 30 collapsed and with x-ray source 68 nestled against a top surface of the unit. The side view of FIG. 5 shows unit 20 configured for travel and shows how, using the collapsed column in this docked position, technician visibility is improved over the conventional fixed vertical column arrangement shown previously in FIGS. 1 and 2.

In each of the embodiments shown in FIGS. 3-18 and following, mobile radiography unit 20 has a wheeled transport frame 22 and has display and control panel components needed for operation, as was described previously with reference to FIG. 1. Sectioned vertical column 30, mounted on frame 22, defines a vertical axis V and has a base section 32 that seats against frame 22 and has a first vertical position relative to axis V, a fixed vertical position in one embodiment. One or more movable sections 34 and 36 are translatable to extend along the vertical axis V, so that boom 70 can be set to a suitable height over a range of possible height settings. In each embodiment, x-ray source 68 can be set to variable vertical and horizontal positions as well as to a range of angular positions about the vertical axis V.

In the embodiment shown in FIGS. 6 through 10, sectioned vertical column 30 has two movable sections, a first, top movable section labeled 36 and a second, middle movable section 34. Sections 34 and 36 are movable in telescoping fashion with respect to stationary base section 32. Boom 70 extends outward from sectioned vertical column 30 and can be rotated into position about vertical axis V. Rotation about axis V can be achieved in a number of ways. In the embodiments shown in FIGS. 6 through 10, sectioned vertical column 30 itself rotates in relation to its transport frame 22. FIG. 11 shows, again from a side view, an alternate embodiment in which column 30 itself does not rotate, but boom 70, mounted at the top of outermost movable section 36, pivots about vertical axis V by rotating about vertical section 36. In yet another embodiment, only the outermost movable section 36, with its attached boom 70, rotates. In each of these embodiments, both rotation about vertical axis V and vertical displacement along the vertical axis can be performed simultaneously.

Figure 6:
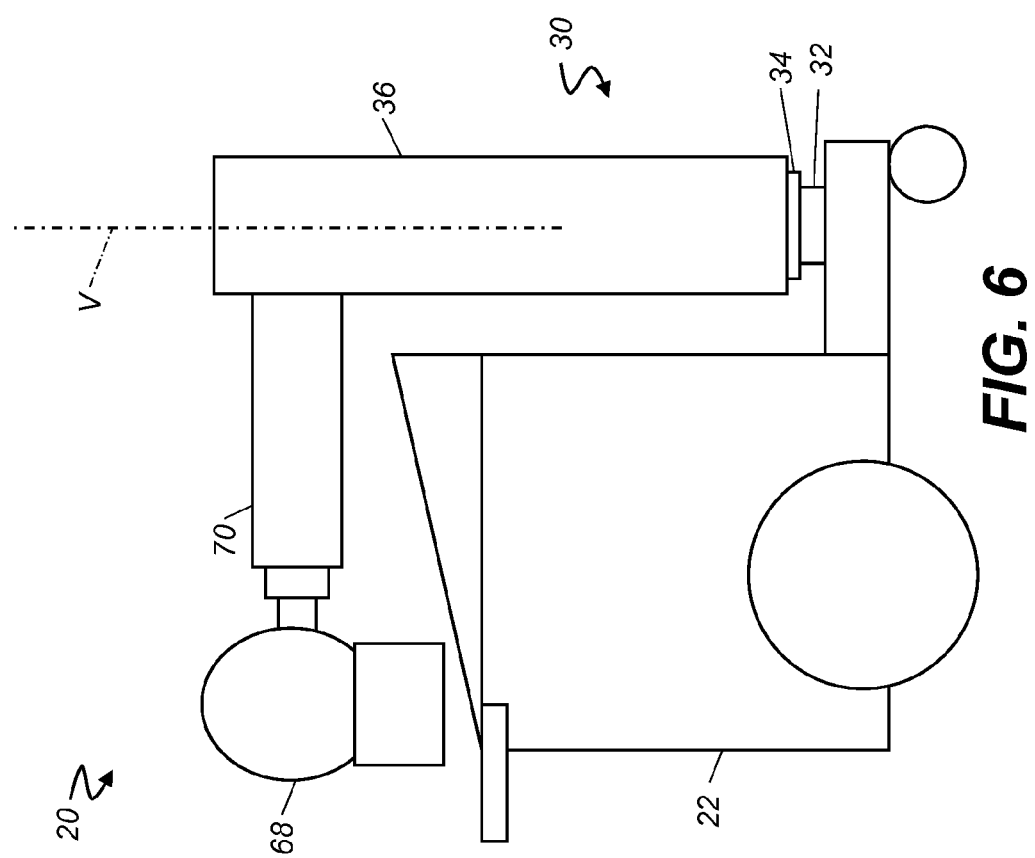
FIG. 6 is a side view showing a mobile radiography unit having a sectioned vertical column and configured for transport.
Figure 7:
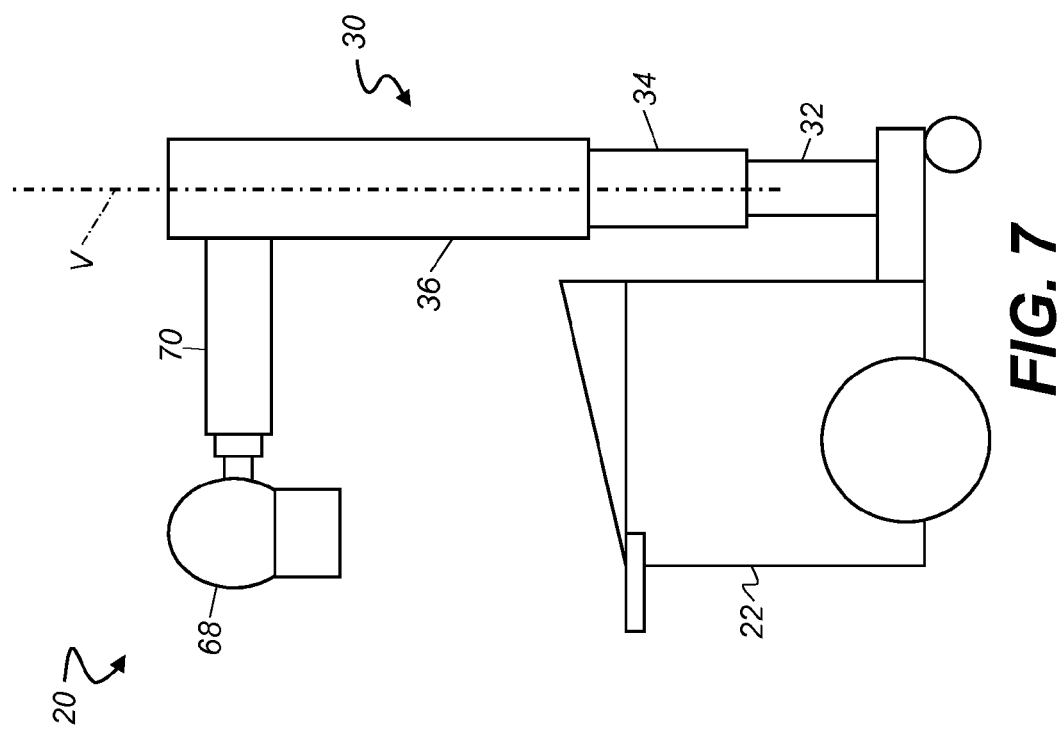
FIG. 7 is a side view showing a mobile radiography unit having a sectioned vertical column and being set up for imaging.
Figure 8:
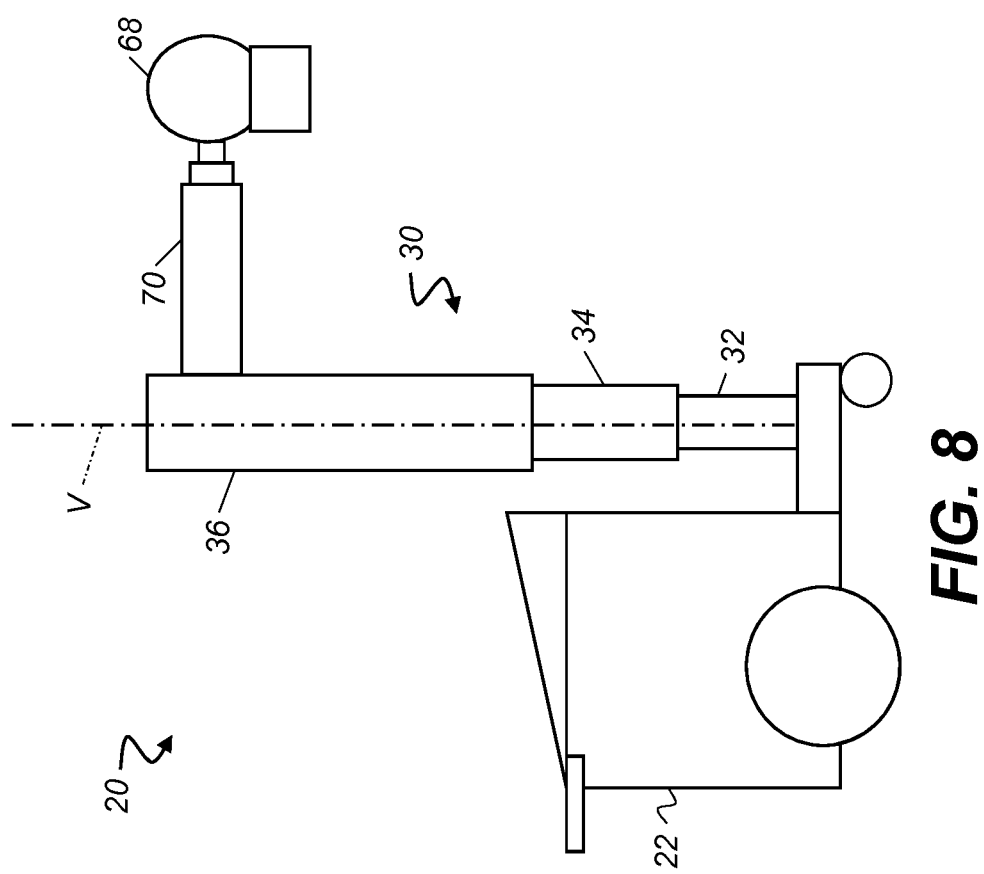
FIG. 8 is a side view showing a mobile radiography unit having a sectioned vertical column that is fully extended for patient imaging.
Figure 9:
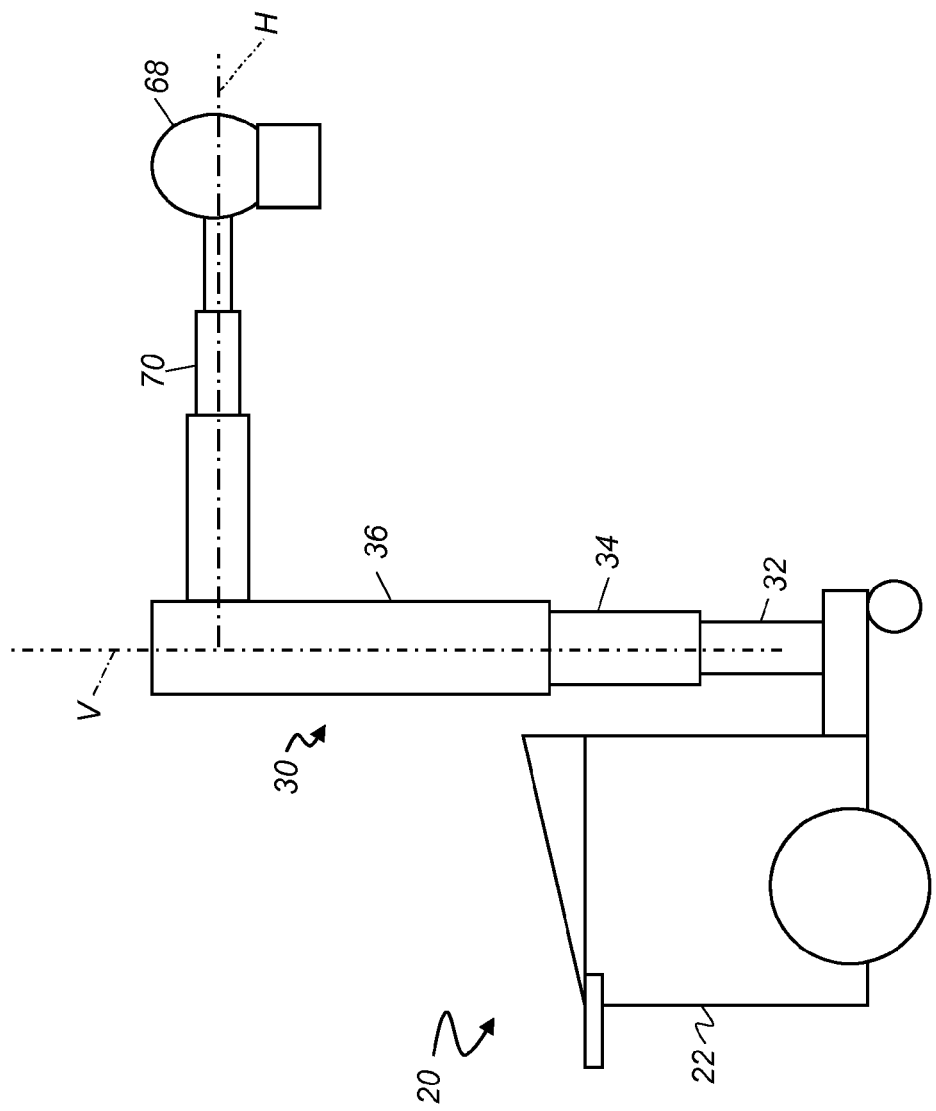
FIG. 9 is a side view showing a mobile radiography unit having a sectioned vertical column that is fully extended for patient imaging with an extended boom for the x-ray source.

In the travel or docked configuration of FIG. 6, sectioned vertical column 30 is collapsed and boom 70 is rotated inward in order to seat x-ray source 68 in a stable position for movement, such as for wheeling from one patient area to another. FIG. 7 shows initial elevation of sectioned vertical column 30 upward from its travel position, readying the unit for deployment. FIG. 8 shows vertical column 30 fully extended, with boom 70 facing outward and with movable sections 34 and 36 at their extreme end of travel. FIG. 9 shows x-ray boom 70 extended orthogonally outward from sectioned vertical column 30 along horizontal axis H, ready for imaging in this position.

Figure 10:
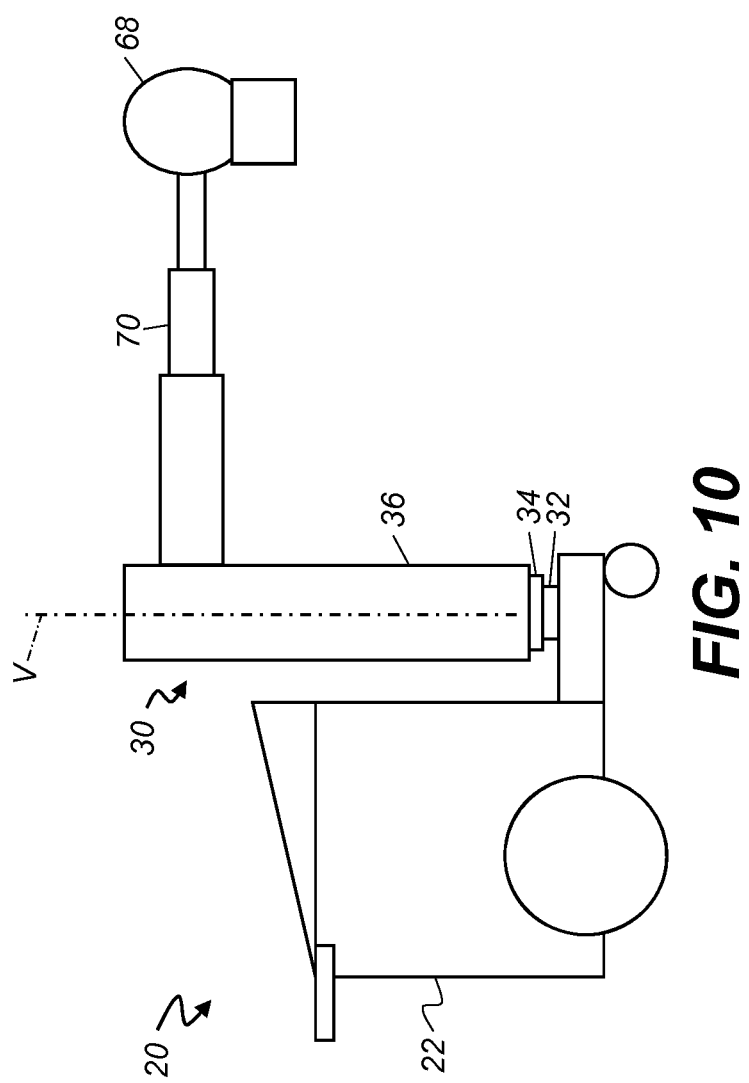
FIG. 10 is a side view showing a mobile radiography unit having a sectioned vertical column that is collapsed for patient imaging of lower extremities.
Figure 11:
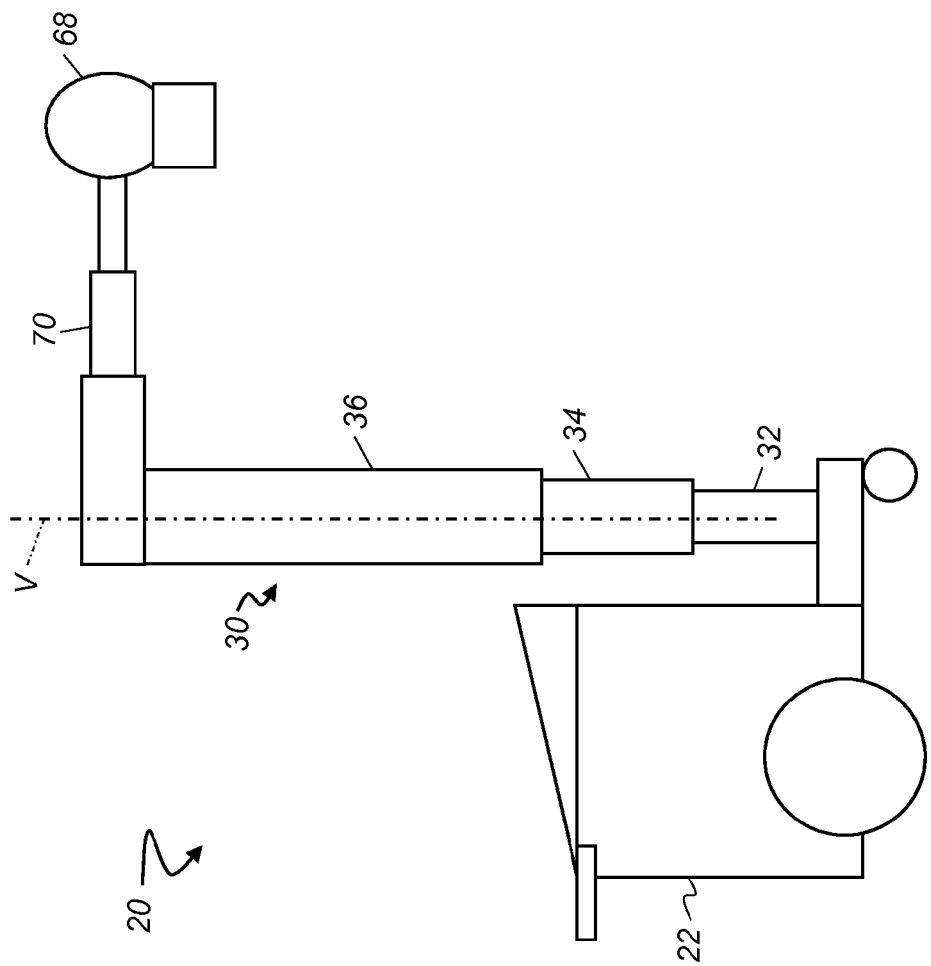
FIG. 11 is a side view showing an alternate embodiment in which the x-ray boom rotates about the top of the vertical column.

With the configuration shown in FIGS. 3-11, the lowest height position for the x-ray source is determined by the length of the outermost movable section 36 and by the position of boom 70 along that length. By way of example, FIG. 10 shows sectioned vertical column 30 in a nearly fully collapsed position, setting x-ray source 68 at low height, near the bottom of its vertical travel range. Using this type of design, the low end of vertical travel is constrained by the position of boom 70 on the outermost section and the length of this section. A lower height can be achieved by increasing the number of movable sections and shortening their respective lengths. It can be appreciated that, beyond a certain number of movable sections, the increased part count and corresponding mechanical complexity can impose some bounds on the practicality of this type of solution for expanding the vertical travel distance to below a certain height.

It is beneficial to allow the fullest possible range of vertical heights for the x-ray source in a portable system, from above shoulder height of the imaging technician to relatively low elevations, such as might be beneficial for imaging the foot or ankle of a patient. As has been shown, this desired height range presents a problem for telescoped column designs. When a telescoped column is fully collapsed, as described with reference to FIG. 10, boom 70, attached to the outermost movable column, can no longer be moved downward. This movement limitation can make the telescoping arrangement less desirable for portable radiography systems.

Embodiments of the present invention address this difficulty by using a boom transport mechanism that cooperates mechanically with a telescoping, sectioned vertical column to allow displacement of the x-ray boom over a wide range of height settings. Advantageously, the operator can easily adjust x-ray boom height, with the weight of column and boom components mechanically balanced so that a substantially uniform amount of effort is needed for height adjustment to any level within the height range.

Figure 12:
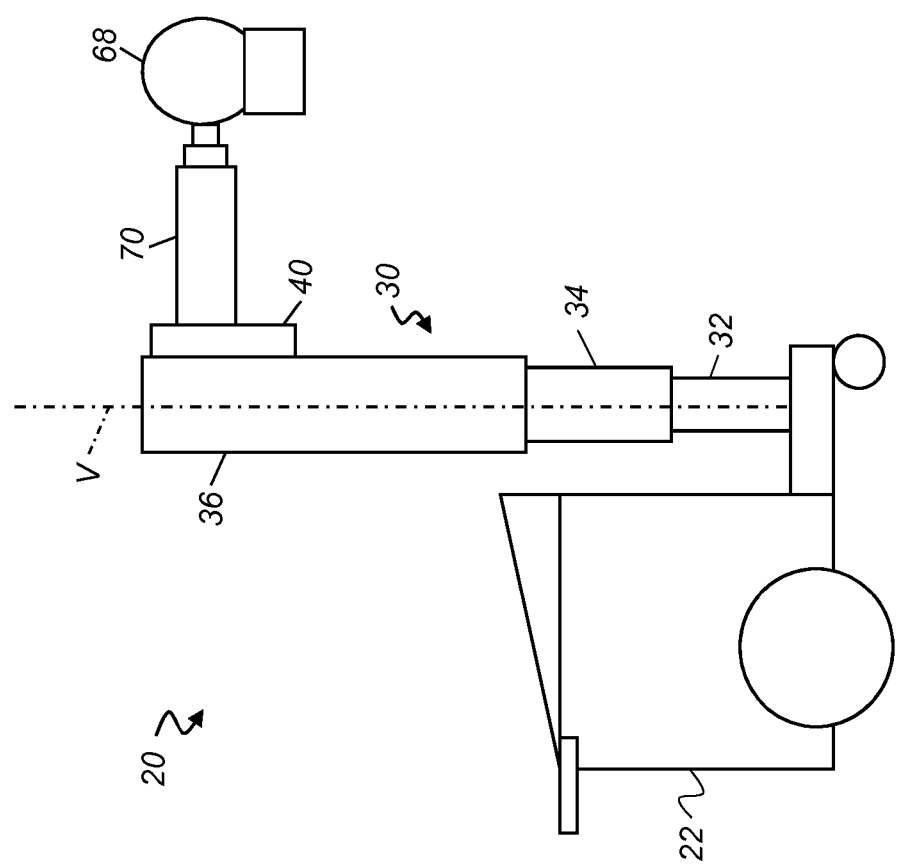
FIG. 12 is a side view that shows an alternate embodiment having a boom transport mechanism for vertical motion of the boom along the length of the uppermost vertical section.
Figure 13:
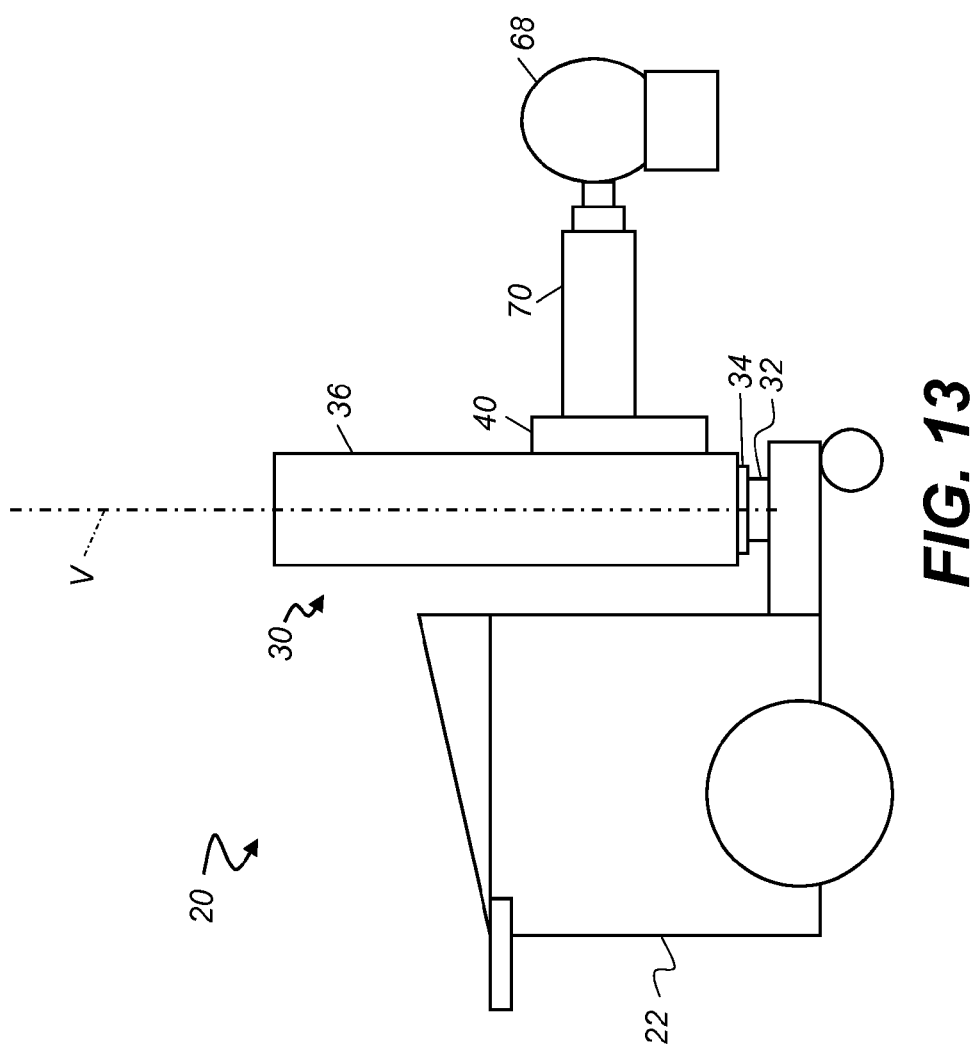
FIG. 13 is a side view that shows how the boom transport mechanism allows lowering of the boom for imaging at low heights.

The side views of FIGS. 12 and 13 show an alternate embodiment of mobile radiography unit 20 in which a boom transport mechanism 40 is mounted on outermost movable section 36 and is actuable to provide the added vertical range needed for imaging with source 68 at a low elevation below the range that is typically feasible with sectioned vertical column 30 fully collapsed when using the embodiment shown in FIG. 10. Boom transport mechanism 40 allows a second mode of vertical displacement for boom 70, so that not only is boom 70 mounted on a vertically collapsible column, but its vertical travel is further permitted for a distance along the length of the outermost movable section.

Figure 14:
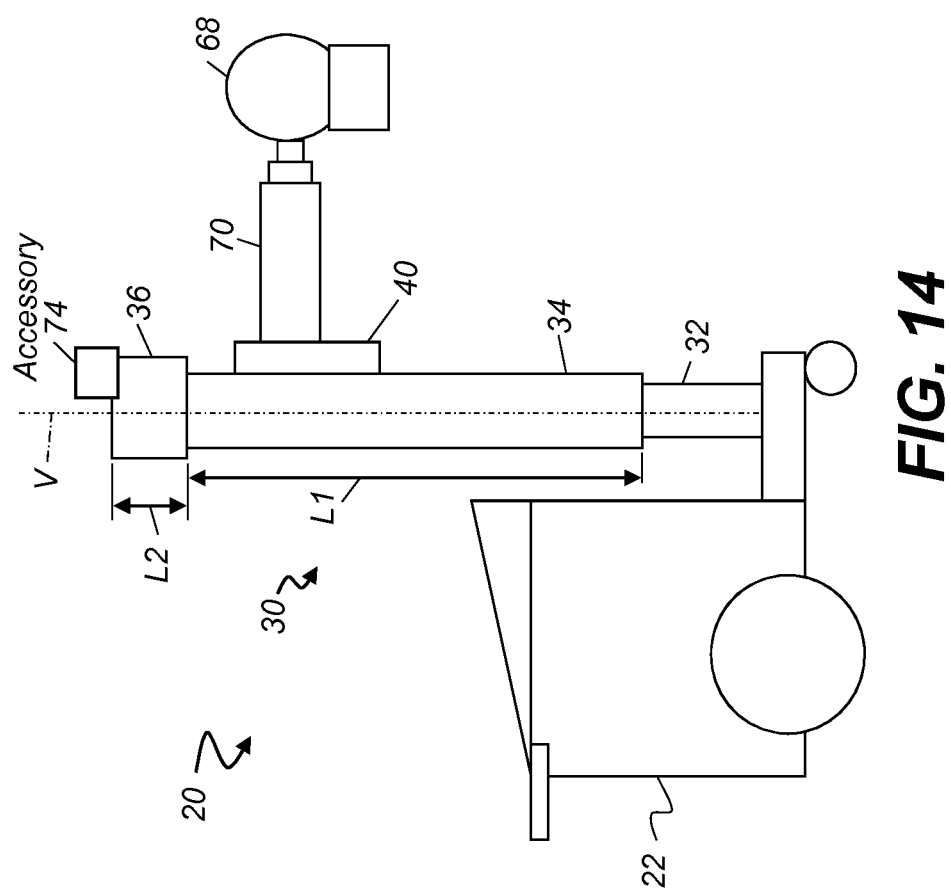
FIG. 14 is a side view showing a mobile radiography unit having a sectioned vertical column with a boom extending from an intermediate section.
Figure 15:
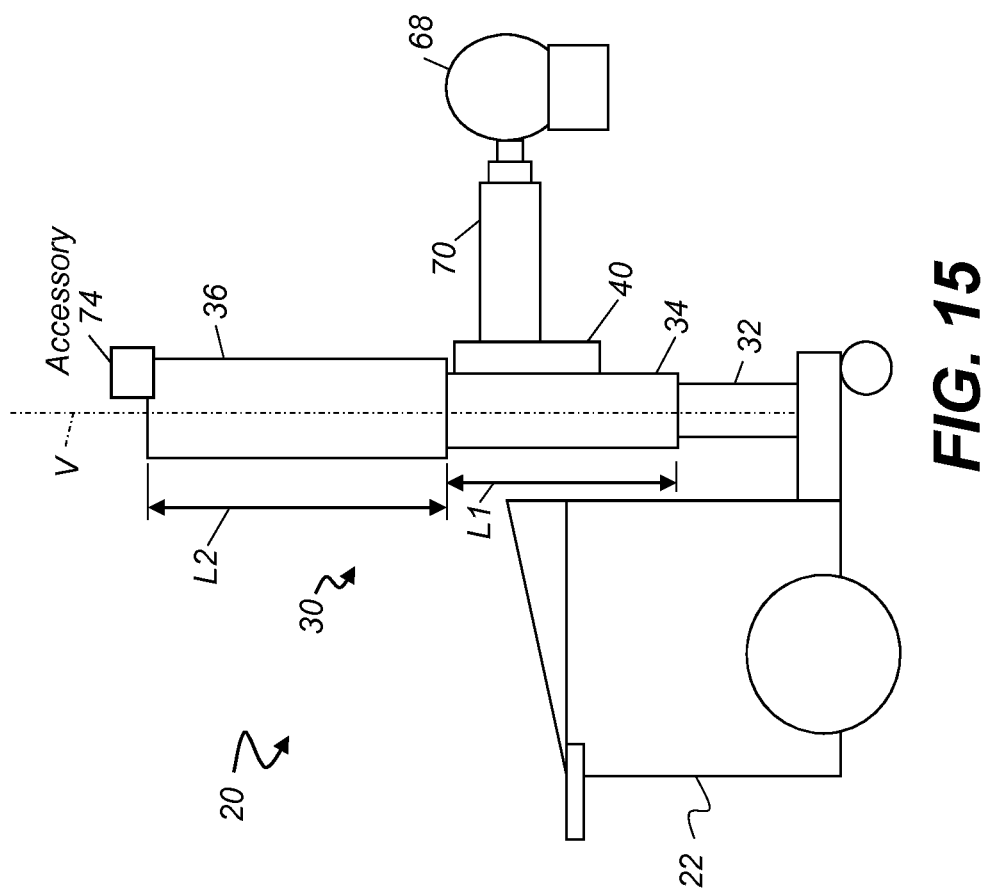
FIG. 15 is a side view showing a mobile radiography unit having a sectioned vertical column with a boom extending from an intermediate section, wherein the intermediate section is shorter than a top section.

It can be appreciated that the apparatus of the present invention admits a number of variations in different embodiments. In the embodiment of FIG. 14, for example, boom apparatus 70 is coupled to intermediate movable section 34 rather than to the top movable section 36. An optional accessory 74, such as a display screen, warning light, or holder, for example, is coupled to movable section 36. Top movable section 36 has a length L2 that varies in different embodiments. In the embodiment shown in FIG. 14, length L2 is smaller than length L1 of intermediate movable section 34. In FIG. 15, length L2 exceeds length L1.

Figure 16:
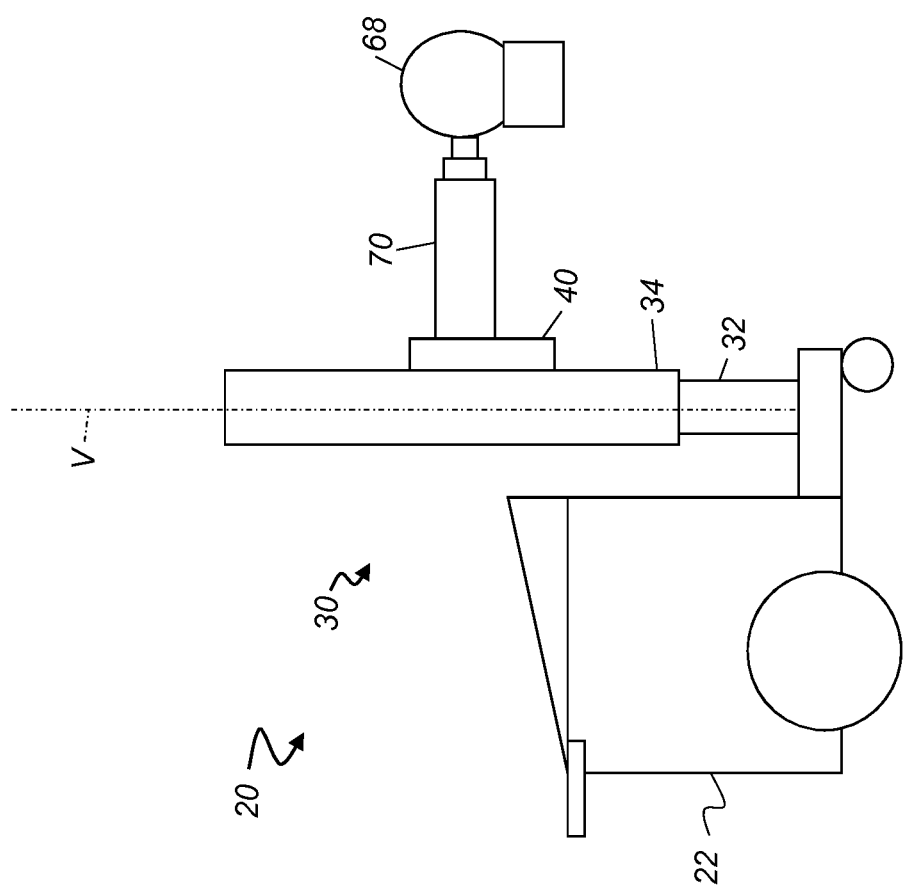
FIG. 16 is a side view showing a mobile radiography unit having a sectioned vertical column with a single movable section.
Figure 17:
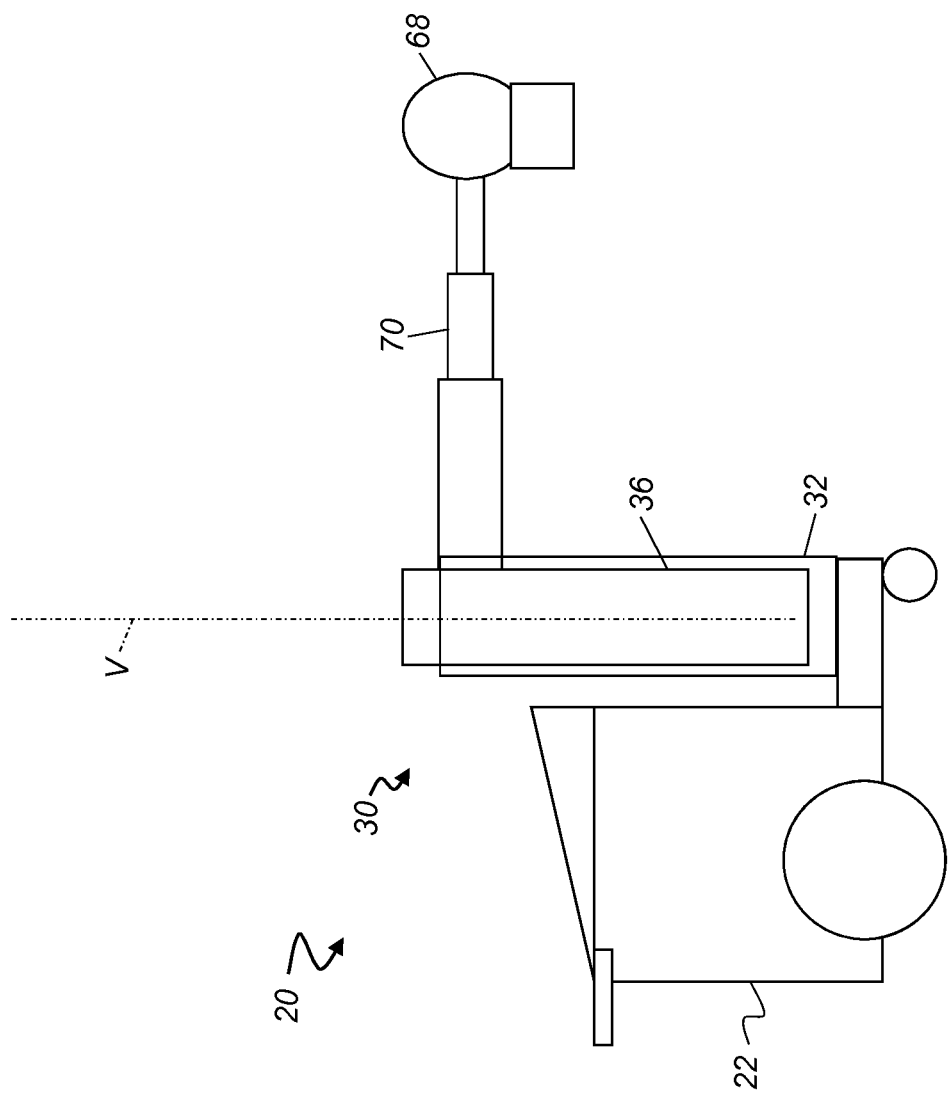
FIG. 17 is a side view showing a mobile radiography unit having a sectioned vertical column with a single movable section, wherein the movable section travels within a fixed outer base section and wherein the sectioned vertical column is collapsed.
Figure 18:
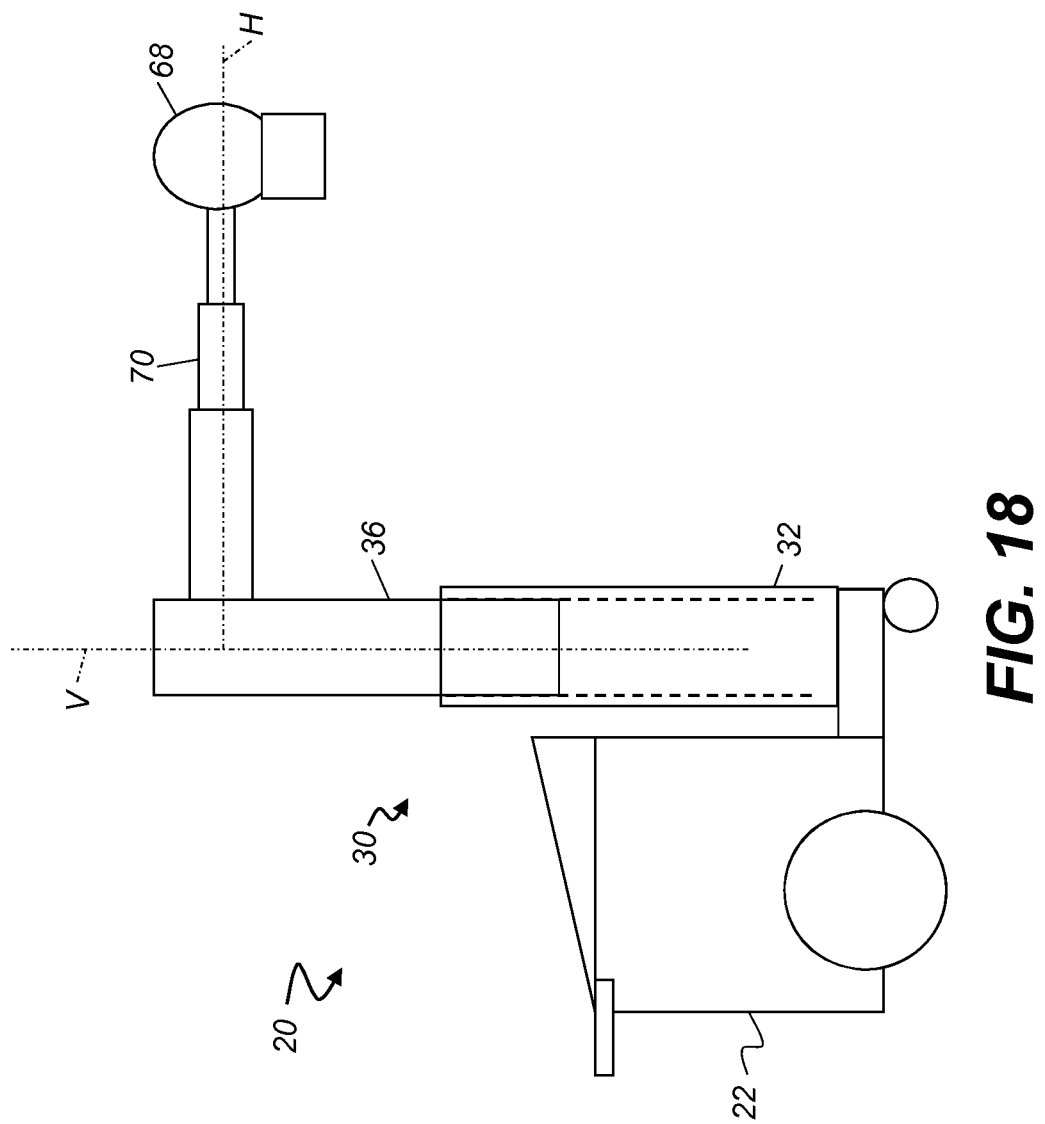
FIG. 18 is a side view showing a mobile radiography unit having a sectioned vertical column with a single movable section, wherein the movable section travels within a fixed outer base section and wherein the sectioned vertical column is extended.
Figure 19:
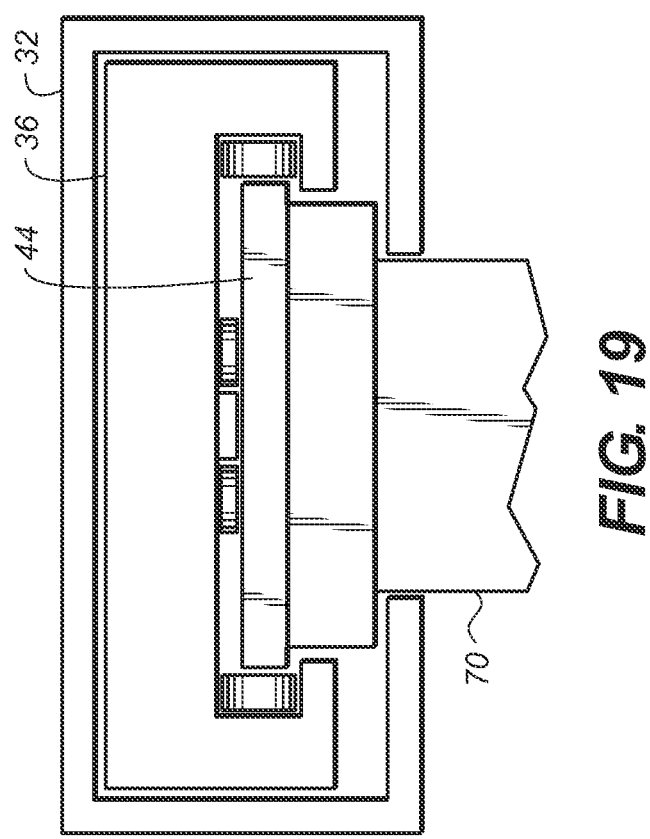
FIG. 19 is a top view cross-section of the sectioned vertical column showing the movable section within the fixed outer base section.

The embodiment of FIG. 16 shows mobile radiography unit 20 having only a single movable section 34 that is fitted on the outside of base section 32, as was shown in embodiments of FIGS. 6-13, for example. In an alternate embodiment, as shown in FIGS. 17 and 18, one or more movable sections 36 are within base section 32; only one movable section 36 is shown in these figures. FIG. 17 shows this sectioned vertical column 30 arrangement in collapsed form. FIG. 18 shows this sectioned vertical column 30 arrangement in extended form. FIG. 19 shows a top view cross-section of sectioned vertical column 30 in the FIGS. 18 and 19 embodiments, showing movable section 36, with carriage 44 supporting boom apparatus 70, within fixed outer base section 32.

Figure 20:
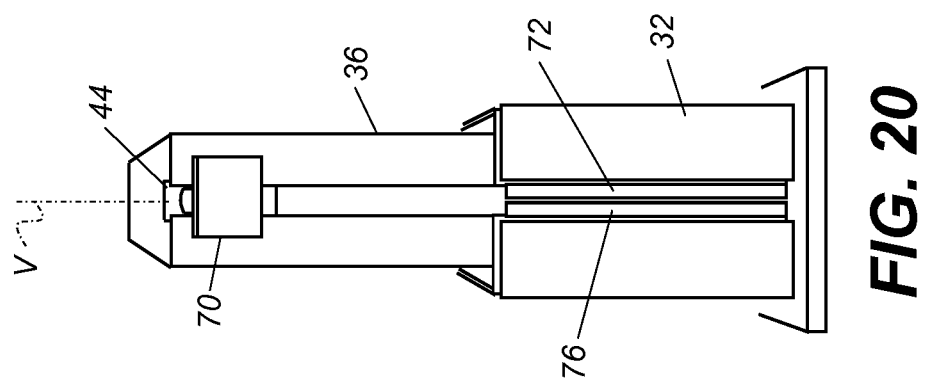
FIG. 20 is a perspective view of the sectioned vertical column of FIG. 24, with boom portions removed for visibility.

FIG. 20 is a perspective view of the sectioned vertical column of FIG. 18, with boom portions removed for better visibility. When movable section 36 travels inside base section 32, as in FIGS. 17-19, a vertical opening 72 is provided in base section 32. Opening 72 allows boom apparatus 70 to travel along the length of base section 32 when in the collapsed column configuration. In one embodiment, a sleeve 76, formed from a resilient material such as rubber or plastic or using brushes or other suitable material, provides a protective covering over opening 72 that allows boom apparatus 70 travel along the opening.

An important design consideration for usability of mobile radiography unit 20 is the ease of movement that is needed for positioning x-ray source 68 in the proper position relative to the patient and to the x-ray detector panel. This is a complex mechanical problem due, in part, to the weight of the x-ray tube and its collimator, which can exceed 100 pounds in some systems. The operator should be able to readily move x-ray source 68 to the needed vertical and horizontal position without undue exertion. In addition, the amount of effort needed to adjust the elevation of x-ray source 68 should be balanced over its full range of vertical displacement, so that substantially no additional effort is needed to adjust the height from one level to another.

Figure 21:
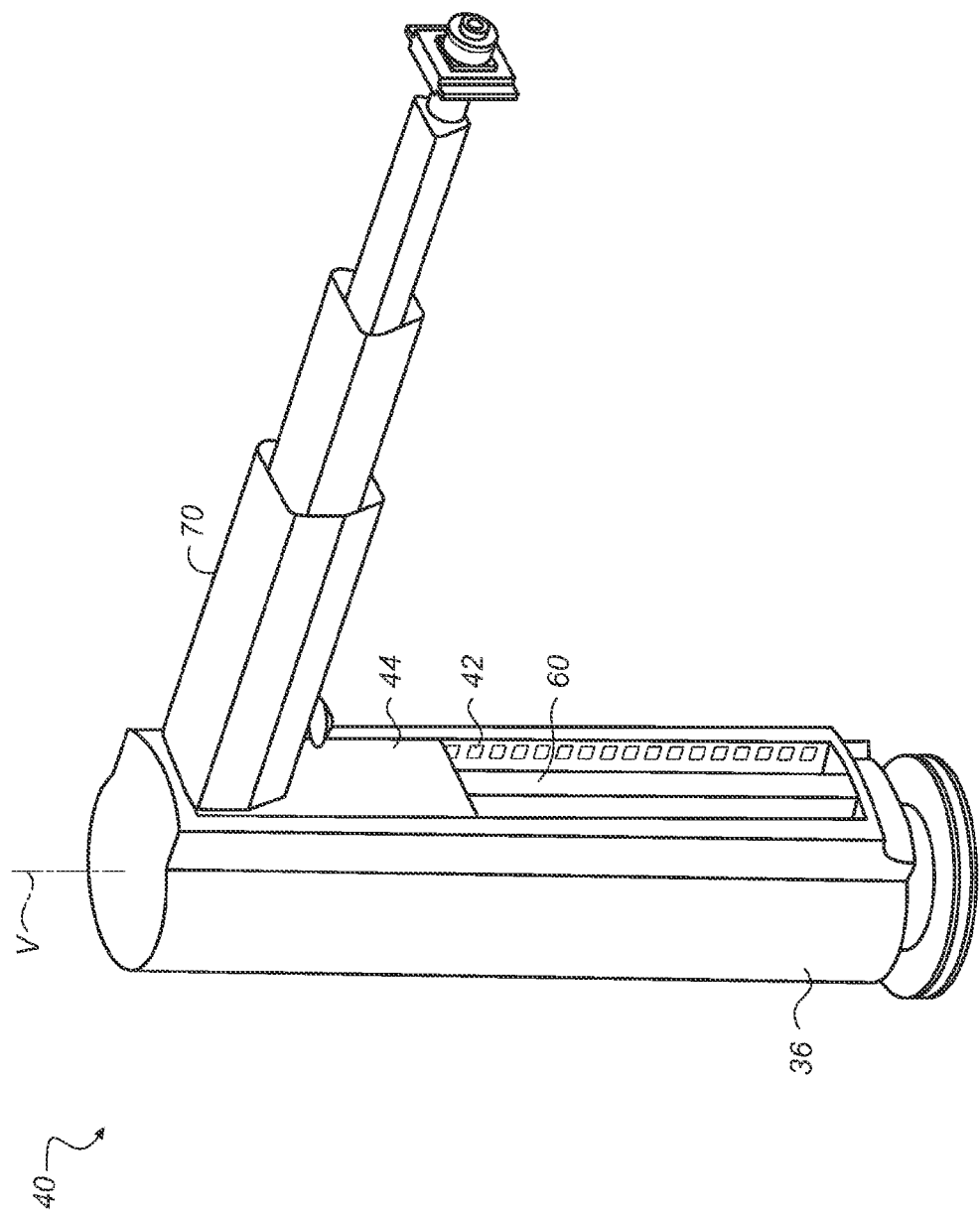
FIG. 21 is a perspective view showing the boom transport on the upper section of the collapsible column, with the transport in an upper position.
Figure 22:
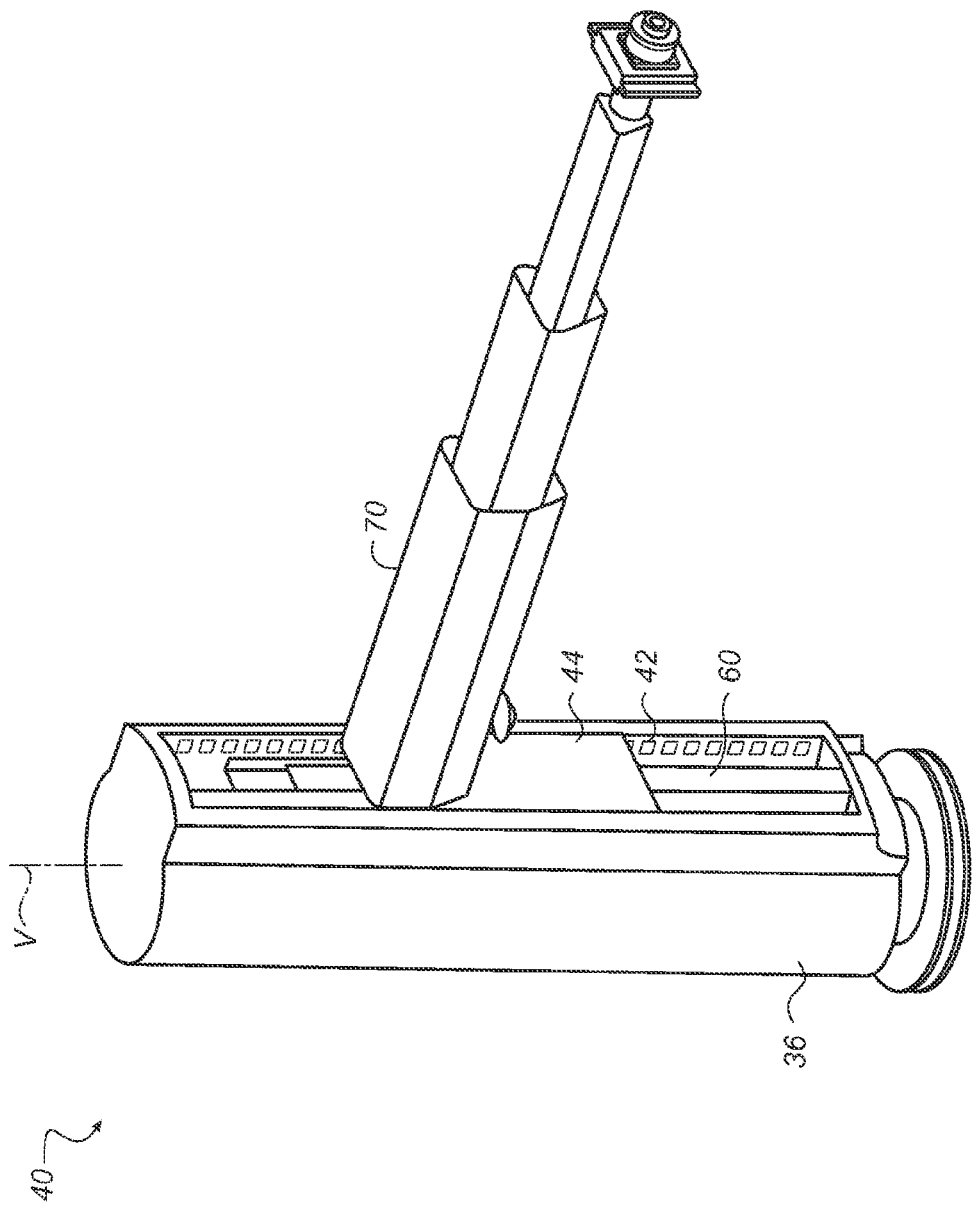
FIG. 22 is a perspective view showing the boom transport on the upper section of the collapsible column, with the transport in a middle position.
Figure 23:
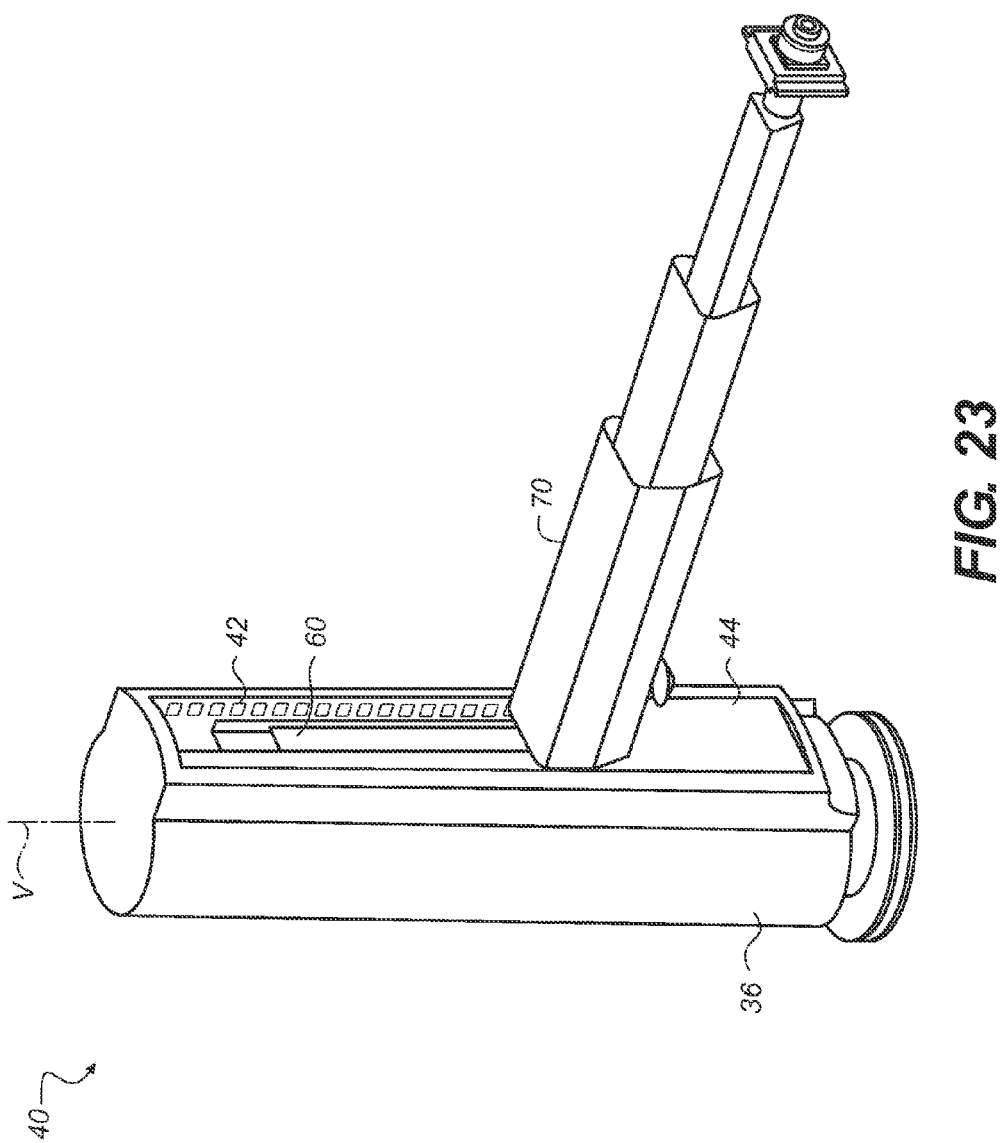
FIG. 23 is a perspective view showing the boom transport on the upper section of the collapsible column, with the transport in a lower position.

The perspective views of FIGS. 21, 22, and 23 show boom transport mechanism 40 and carriage mechanism 44 in different vertical positions along upper section 36. In these figures, boom transport mechanism 40 is coupled to section 36 by wheeled carriage mechanism 44 that is movable within a track.

Boom transport mechanism 40, shown in schematic detail in top and side views of FIGS. 24A and 24B, respectively, has a series of wheels 54 that rotate within a track 42 to provide vertical displacement. Four wheels are used for this function in the embodiment shown in FIGS. 24A and 24B. Two additional pairs of wheels 58 rotate in an orthogonal direction against a centering block 60 in order to constrain unwanted side-to-side movement of boom 70 relative to the vertical axis. It can be appreciated that alternative embodiments can be used for boom transport mechanism movement, including the use of one or more linear bearings, for example.

FIGS. 25A and 25B show schematically how a counterweight 80 is deployed in order to provide a lifting force for boom apparatus 70 in an embodiment of the present invention that uses a sectioned vertical column. Counterweight 80 is operatively coupled to boom apparatus 70 to support displacement of boom apparatus 70 to any of a plurality of vertical positions. FIG. 25A shows boom apparatus 70 at a low elevation, with the section column collapsed, such as might be used for imaging a patient's foot or lower leg, for example. FIG. 25B shows the column in an extended position, with movable section 34 extended from base section 32 and boom apparatus 70 raised toward its maximum height. Counterweight 80 is operatively coupled to boom apparatus 70 by means of a pulley 82 and a cable 90. In cooperation with boom apparatus 70 movement, counterweight 80 is vertically displaced along a shaft 78, a cavity that extends within the column, in the direction of the vertical axis V.

In the embodiment shown in FIGS. 25A and 25B, a force S is provided by a motor 88 or other actuator or by a spring to provide a counterbalance force for lifting movable section 34 to a vertical position. To provide this force, a cable 92 is routed around a pulley 84 and through wheels 86 to motor 88 or other actuator. A mechanical ground to movable section 34 is shown at G.

While FIGS. 25A and 25B show component interrelations and principles schematically, there are some practical problems with the idealized arrangement that is shown. Among these difficulties are dimensional limitations. Counterweight 80 travels within a shaft that is internal to the sectioned column, with the column dimensionally sized for portability. This sets some constraints on the overall width dimension (that is, dimensions orthogonal to the vertical axis V) that can be allowed for this heavy counterweight 80 component, whose weight depends both on its volume and on the mass of its component material. Lead is conventionally used for counterweights, but other dense materials that are considered less hazardous are preferred and can be used if additional volume is provided. In addition to volume constraints, it is preferable that the operator be shielded from possible inadvertent contact against moving parts such as internal pulleys, cables, and related moving components that relate to boom or column movement. While the embodiment shown in FIGS. 25A and 25B is for a sectioned vertical column, the same counterweight displacement arrangement can apply for an embodiment using a single column element, where the column height is fixed.

Figure 26B:
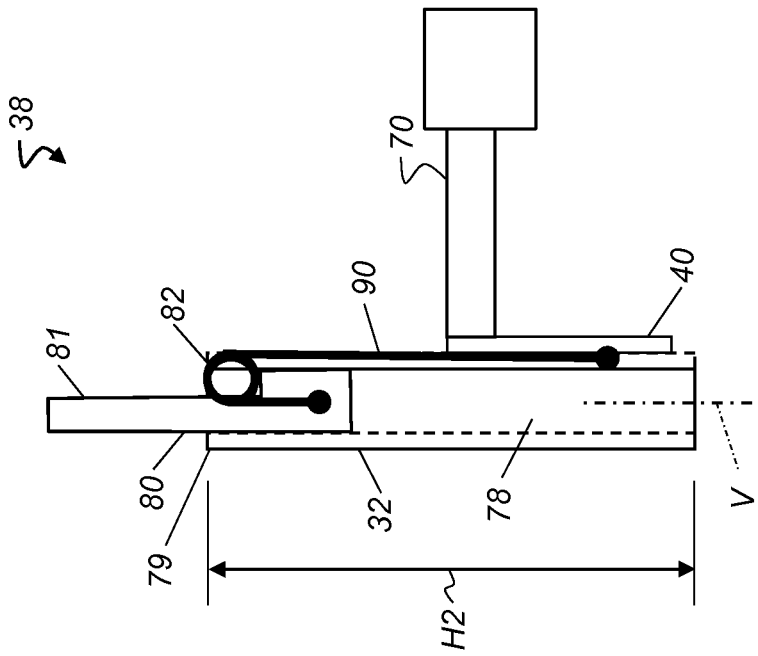
FIGS. 26A and 26B show schematically the use of a counterweight that is elongated, according to one embodiment of the present invention, with the boom apparatus in raised and lowered positions, respectively.
Figure 26A:
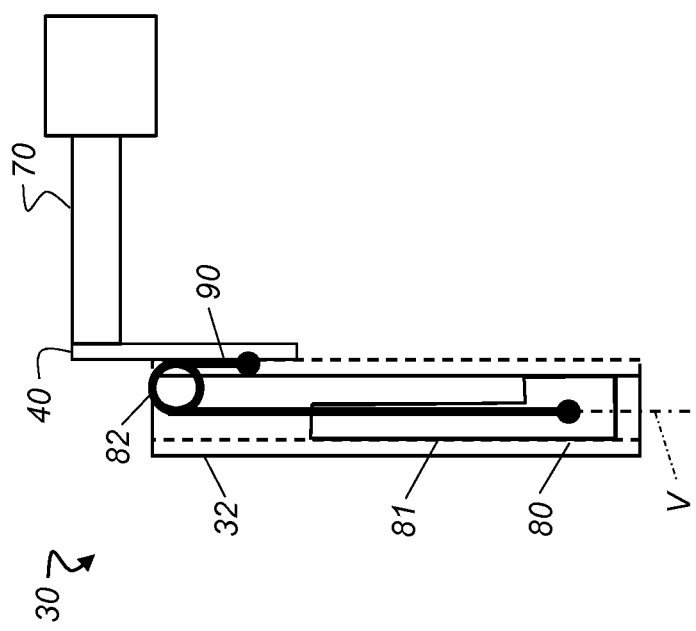
Figure 26D:
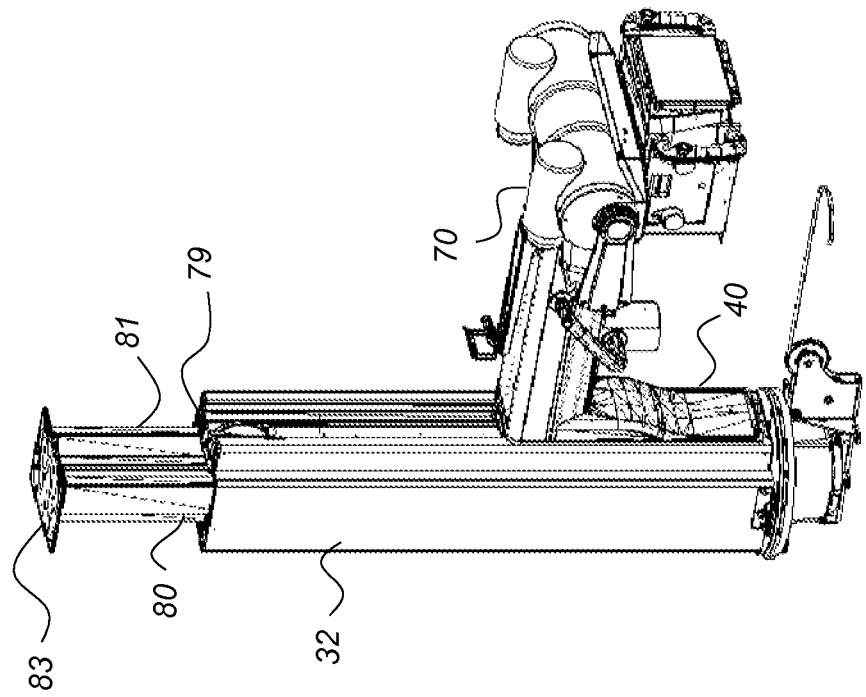
FIGS. 26C and 26D are perspective views that show boom apparatus in the raised and lowered position and show the counterweight element extending upwards when the boom is lowered.
Figure 26C:
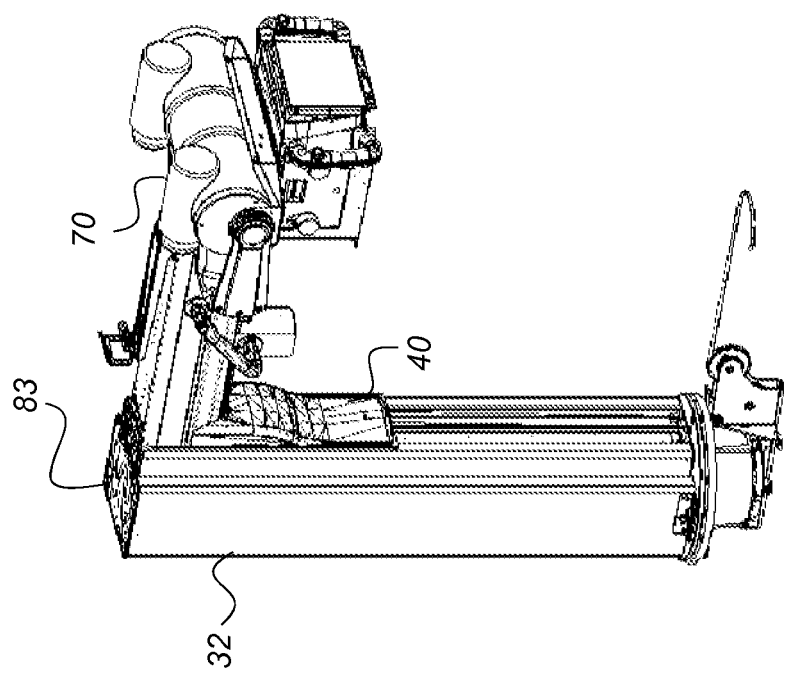

As shown schematically in FIGS. 26A and 26B, and in perspective views in corresponding FIGS. 26C and 26D, embodiments of the present invention address the problem of limited width dimension by extending the length of counterweight 80 in the vertical direction. An extended section 81, formed as part of counterweight 80, such as part of a single casting, adds volume to counterweight 80 in an upward vertical direction. FIGS. 26A and 26B show a vertical column 38 in one embodiment, consisting of base section 32 only and having no movable sections. As shown in FIGS. 26B and 26D, with boom 70 lowered, extended section 81 of counterweight 80 can protrude or extend above shaft 78, whose top edge is defined by a top edge 79 of vertical column 38. An optional cap 83 is provided to cover shaft 78 in the embodiment of FIGS. 26C and 26D. FIG. 26B shows a shaft height H2, in an embodiment in which shaft 78 extends fully through stationary column 32. In an alternate embodiment, shaft 78 extends only partway through column 32. In arrangements with multiple sections, the top of shaft 78 is defined by the top edge 79 of the uppermost section of the column.

The use of increased height for counterweight 80 has particular value in embodiments where the vertical column has one or more movable sections. FIGS. 27A, 27B, and 27C show an alternate embodiment using a sectioned vertical column 30 with base section 32 and movable section 34. As these figures show, the combination of variable column height and variable counterweight 80 position allows a number of possible combinations for achieving the same height H1 for boom apparatus 70. In FIG. 27A, for example, movable section 34 is extended upwards and extended section 81 of counterweight 80 protrudes from the top of shaft 78 by a distance D1 when height H1 is achieved. In FIG. 27B, the same height H1 is reached with movable section 34 somewhat less extended; here, extended section 81 of counterweight 80 protrudes from the top of shaft 78 by a lesser distance D2. In FIG. 27C, the column is collapsed and, with boom 70 at the position shown relative to movable section 34, counterweight 80 is wholly enclosed within shaft 78, with no portion protruding above top edge 79. As can be seen from this example, there can be any number of possible arrangements of column and counterweight 80 components used for achieving intermediate heights of boom apparatus 70 with sectioned vertical column 30. An optional brake 52 is also provided that, when actuated, constrains or prevents vertical movement of movable section 34.

With respect to FIGS. 25A through 27C, it can be appreciated that other arrangements of component weights and pulley configurations are possible, as well as mechanical configurations using counterweights or various types of electromechanical or hydraulic actuators, for example. As shown in the examples given above, vertical column 30 can have one section only so that it is of a fixed height, or can have one or more movable sections to allow variable height. Various types of mechanical brake configurations are also possible and may be provided for helping to stabilize vertical movement of column sections or of the boom apparatus 70 itself.

Figure 28A:
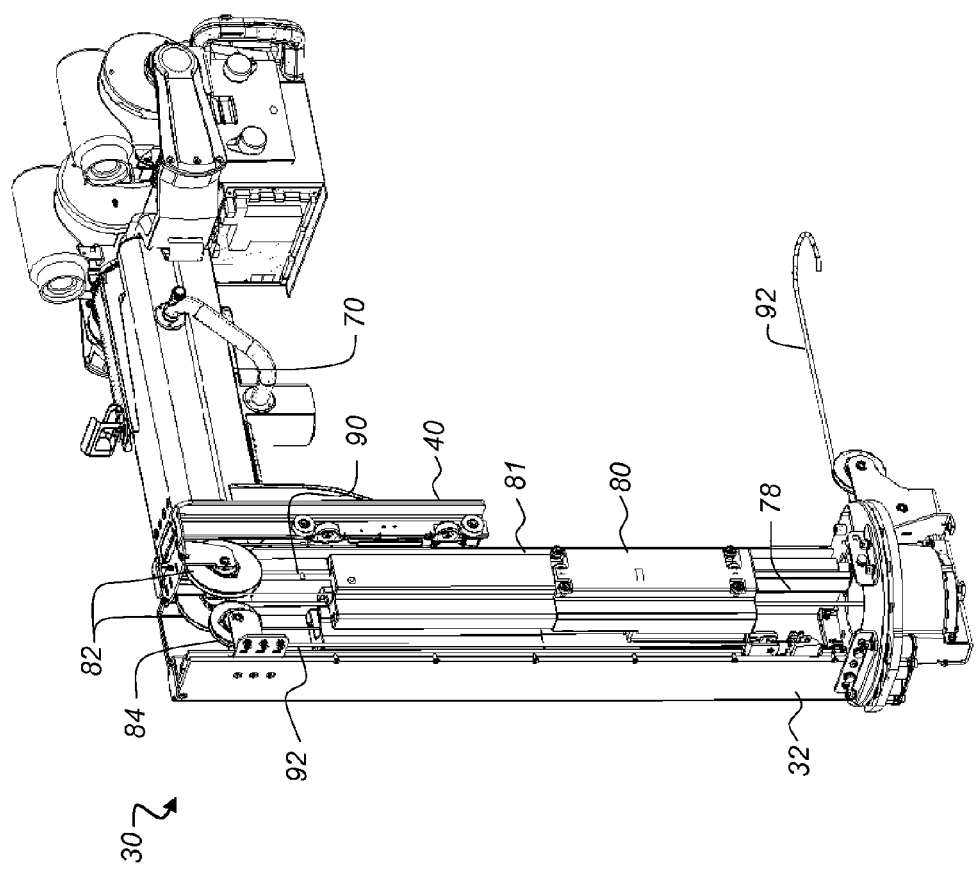
FIGS. 28A, 28B, and 28C are partial cutaway views that show counterweight and support components for lifting the boom apparatus.
Figure 28B:
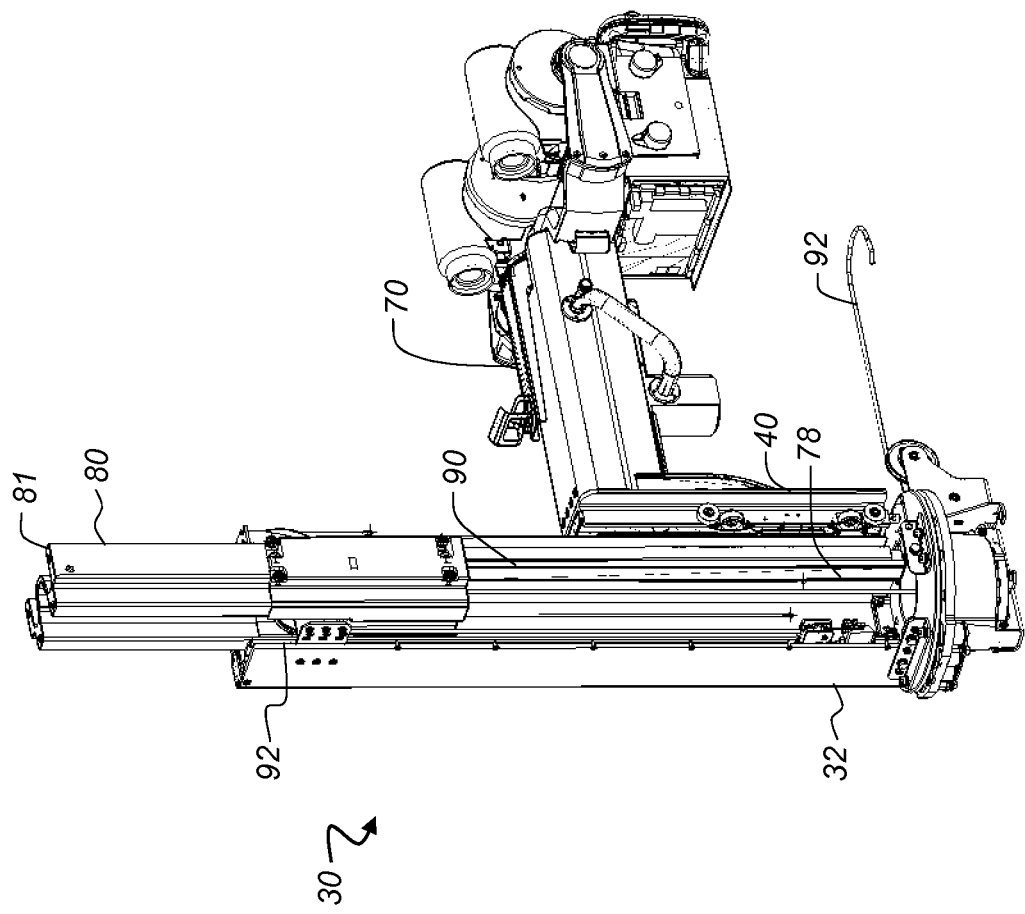
Figure 28C:
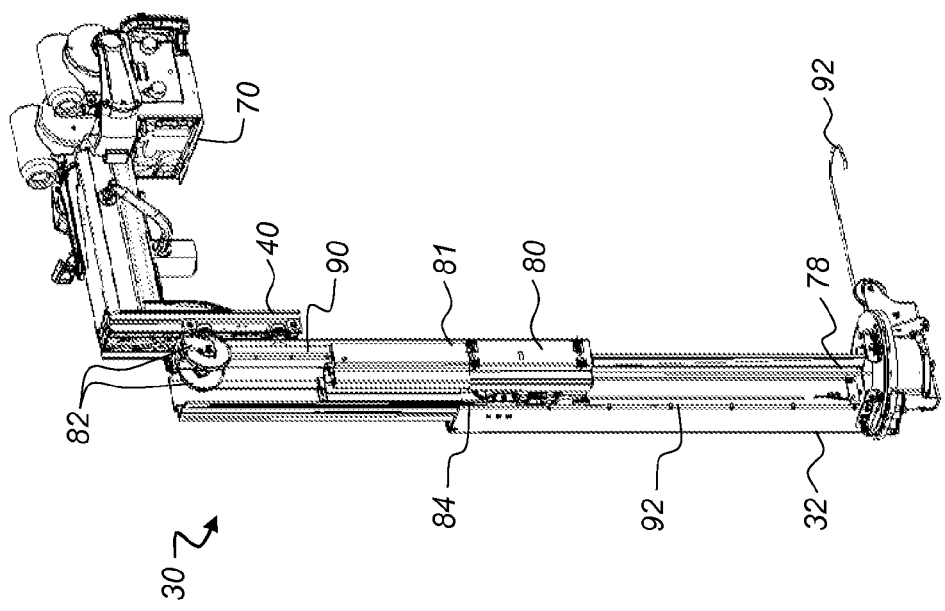

The partial cutaway views of FIGS. 28A, 28B, and 28C show internal components of sectioned vertical column 30 that support lifting and lowering of boom apparatus 70 and show counterweight 80 at a number of different travel positions within shaft 78. In FIG. 28A, boom apparatus 70 is at a height that is approximately level with vertical column 30 when not extended. Counterweight 80 extends vertically over a considerable portion of shaft 78 in the embodiment shown. In FIG. 28B, boom apparatus 70 is lowered to near the lowest point of travel, so that extended section 81 protrudes from the top of the column. FIG. 28C shows movable section 34 extended, with boom apparatus 70 raised to near its highest position relative to movable section 34. The embodiment shown in FIGS. 28A, 28B, and 28C has two pulleys 82 for lifting and lowering counterweight 80 using two corresponding cables 90, as shown in more detail subsequently.

Figure 29A:
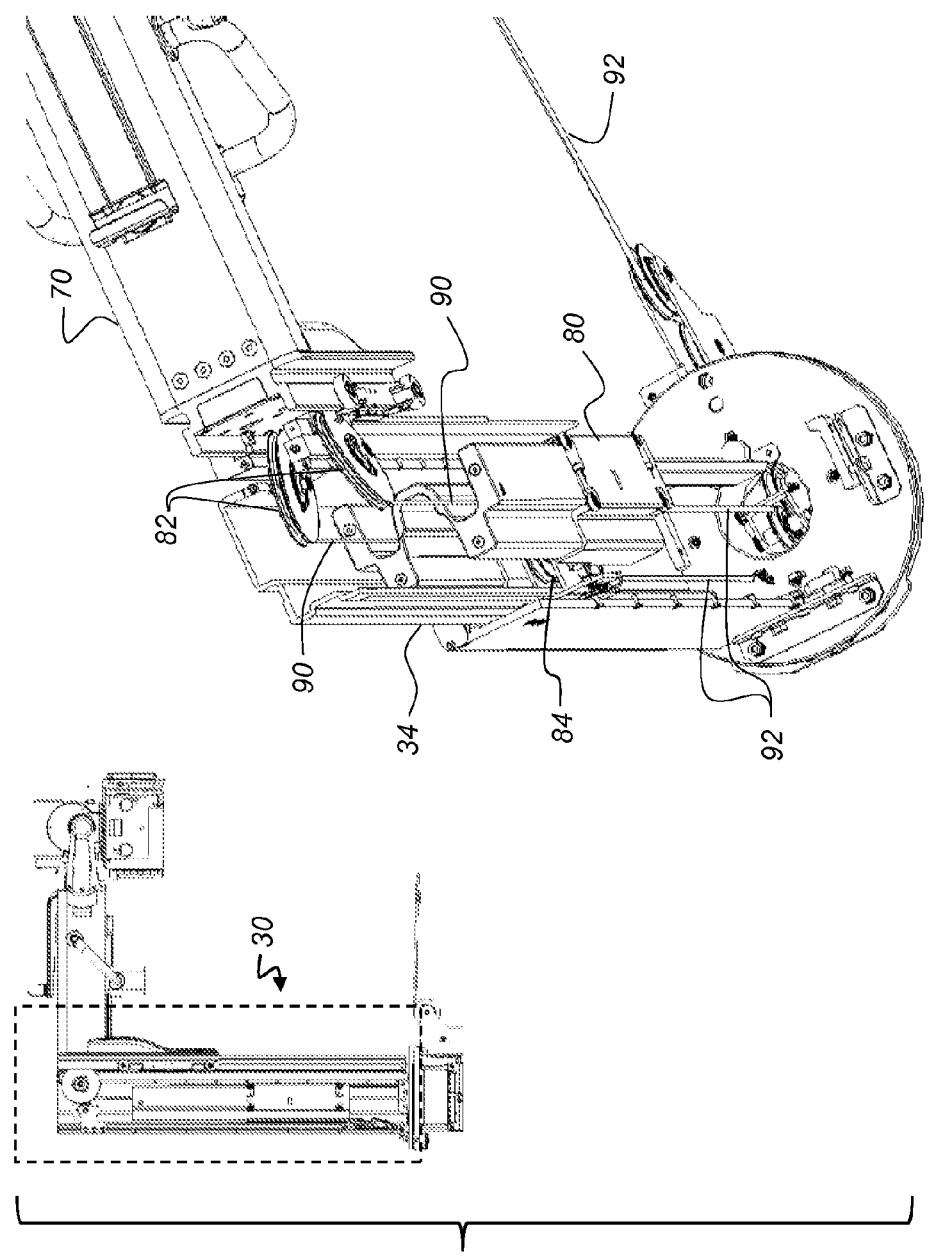
FIGS. 29A and 29B are perspective views that show internal components used for raising and lowering the boom apparatus.
Figure 29B:
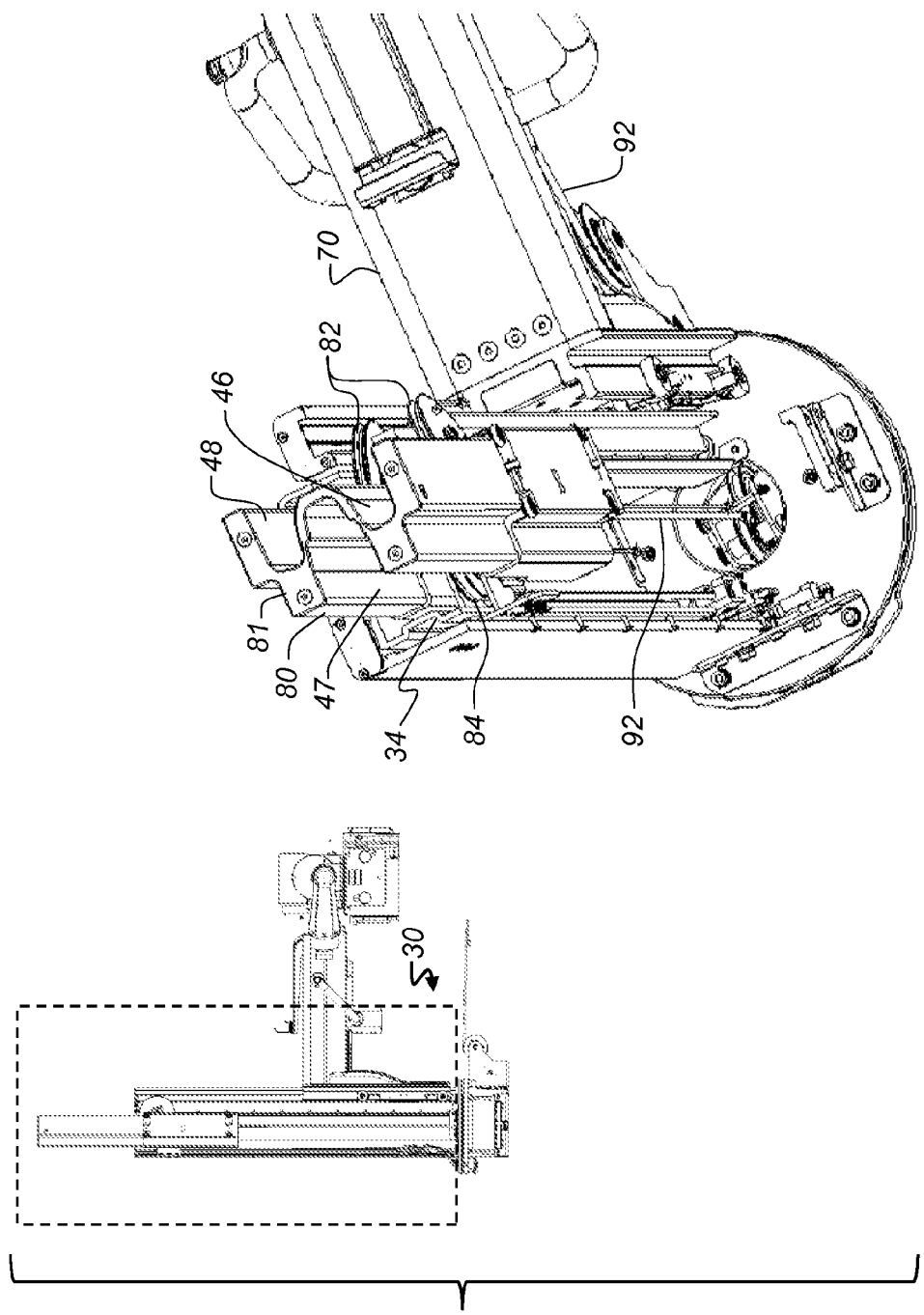
Figure 29C:
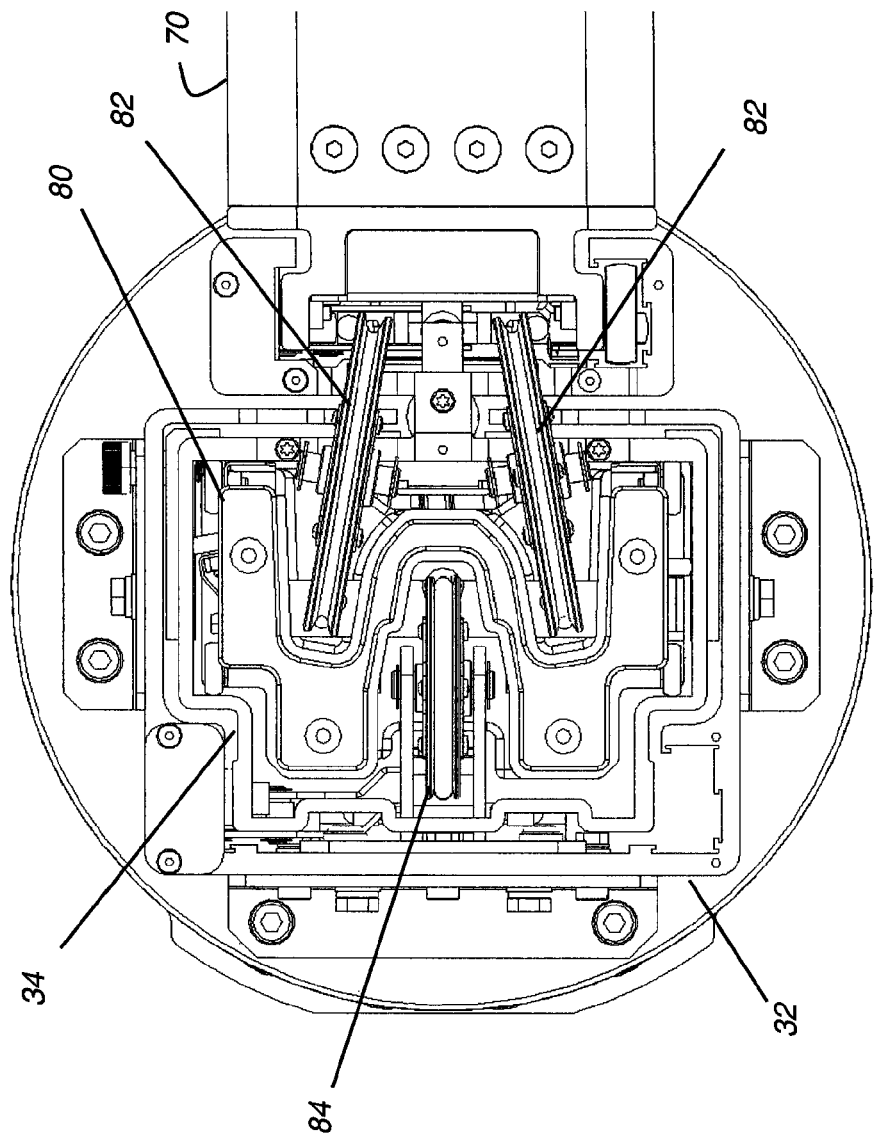
FIG. 29C is a top view that shows internal components used for raising and lowering the boom apparatus.

FIGS. 29A, 29B, and 29C are perspective views that show pulley, cable, and counterweight components for a sectioned column 30 in greater detail. FIG. 29A shows components for this function with boom apparatus 70 at a raised position and sectioned vertical column 30 extended. Counterweight 80 is lowered to allow better visibility of pulleys 82 and cables 90. Pulleys 82 for boom apparatus 70 are obliquely disposed with respect to each other, in order to allow counterweight 80 to travel at least partly past them, as shown in FIG. 29B, for example. Counterweight 80 is featured with a number of vertical grooves, shown in more detail subsequently, that allow movement of counterweight 80 past pulleys 82 within the shaft and allow vertical travel of cables 90 within the shaft.

The top view of FIG. 29C shows this oblique arrangement of pulleys 82 and the relative position of pulley 84 that is part of the apparatus for lifting movable section 34. This arrangement allows the two pulleys 82 and pulley 84 to support corresponding cables 90 and 92 that also travel through shaft 78. Cables 90 are coupled to counterweight 80, toward the bottom of this component.

It should be noted that the mechanical arrangement of cable 92 and pulley 84 shown in FIGS. 28A through 29C allows rotation of sectioned vertical column 30 about vertical axis V. Where column shape permits, this arrangement can also allow at least partial rotation of movable section 34 about base section 32, as noted previously.

In the sectioned vertical column embodiment of FIGS. 29A-29C, component packaging requirements are very tight, and counterweight and pulley elements must be fitted around each other in order to allow counterweight travel, increase counterweight volume, and support vertical movement of section 36 at the same time, along with counterbalance components for the movable section 36. Using conventional design approaches, the travel path of cable 92 needed for moving section 36 would constrain the amount of volume available for counterweight 80 within shaft 78, requiring one of the vertical grooves to extend the full length of counterweight 80. This would be needed even though the travel path of counterweight 80 does not extend past the position of pulley 84. The embodiment of counterweight 80 shown in FIG. 29A and following addresses this problem without requiring a full-length vertical groove as is used to work past each pulley. Instead, cable 92 extends through a hole formed in counterweight 80 so that its travel path runs inside counterweight 80, rather than alongside the counterweight. This feature allows components that provide both boom 70 transport counterweight force and movable column 36 translation counterbalance force to work without interfering with each other within the narrow confines of shaft 78.

Figure 30B:
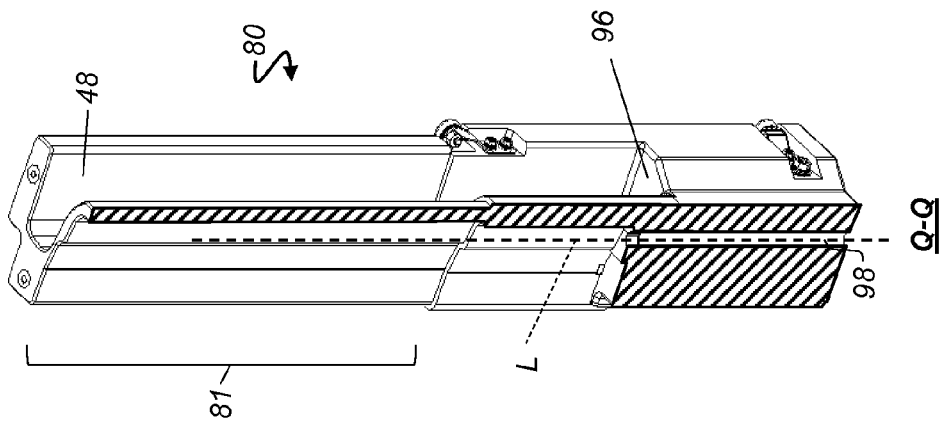
FIG. 30B is a sectioned view of the counterweight shown in FIG. 30A.
Figure 30A:
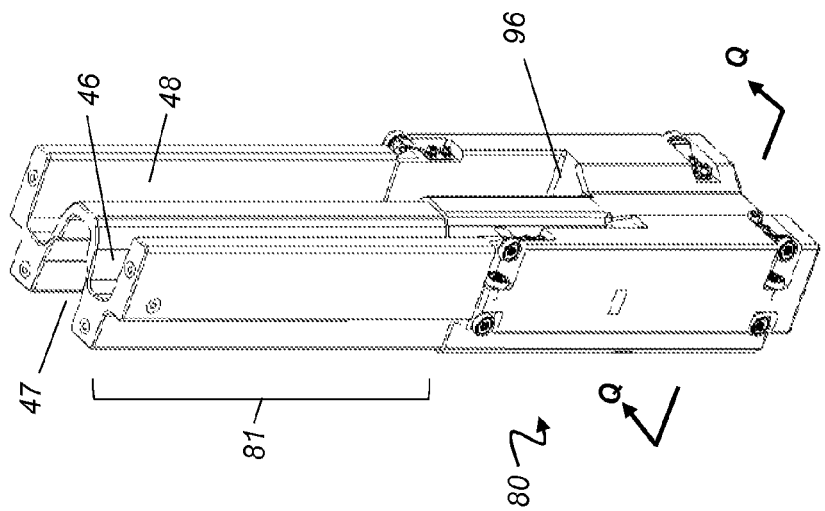
FIG. 30A is a perspective view of a counterweight according to an embodiment of the present invention.

FIG. 30A is a perspective view of counterweight 80 consistent with an embodiment of the present invention, formed as a single casting. Vertical grooves 46 and 48 extend partially through counterweight 80 from the top to a shelf 96. With this arrangement, vertical grooves 46 and 48 allow upward vertical movement within the shaft of at least some of extended portion 81 past pulleys 82, as is shown in FIG. 29B, for example. A vertical groove 47 that extends along the opposite side of counterweight 80 allows upward vertical movement of at least some of extended portion 81 past pulley 84, as is also shown in FIG. 29B.

Figure 30C:
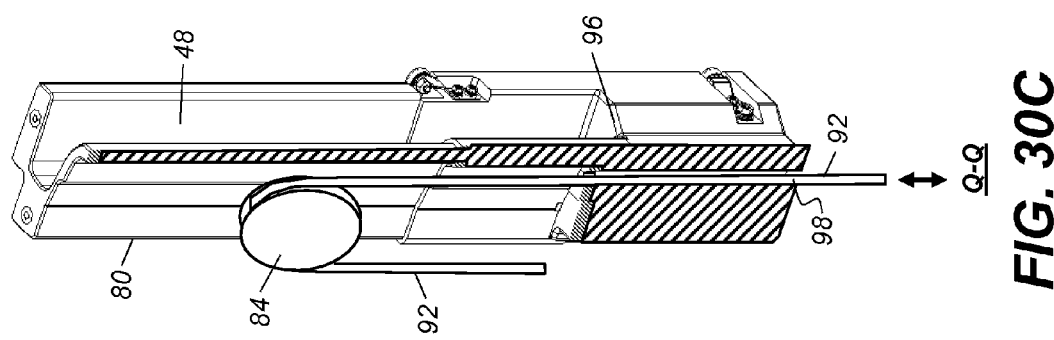
FIG. 30C is a sectioned view of the counterweight shown in FIG. 30B showing the path of a column transport apparatus cable through a cavity in the counterweight.
Figure 30D:
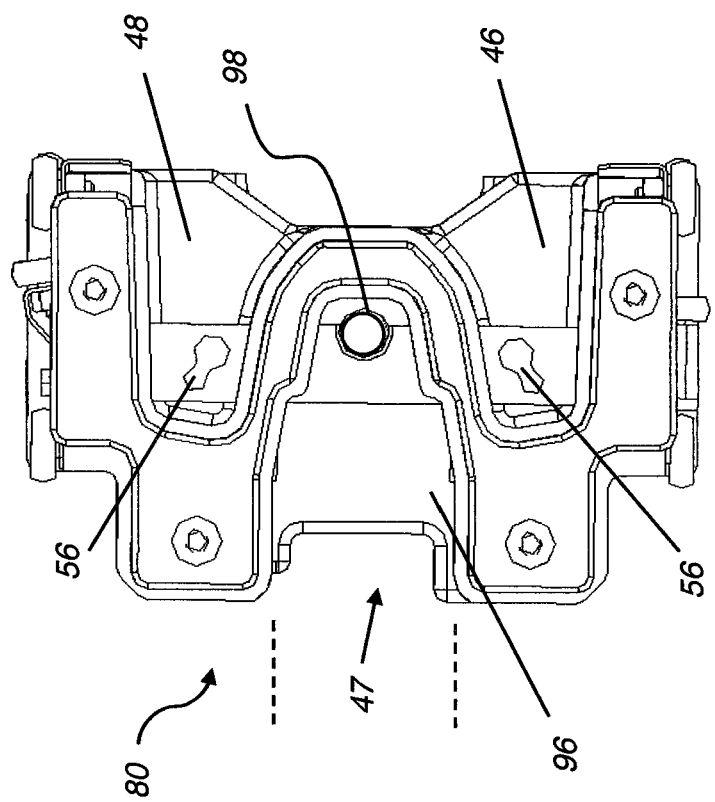
FIG. 30D is a top view of the counterweight shown in FIGS. 30A and 30B.

FIG. 30B is a sectioned view of the counterweight shown in FIG. 30A, taken along section line Q-Q as indicated in FIG. 30A. As indicated by a dashed line L, cable 92 from pulley 84 travels inside counterweight 80 during vertical movement of counterweight 80, through a cavity 98 that is formed in counterweight 80. FIG. 30C shows a portion of the path of cable 92 relative to counterweight 80 at one position, with the cable 92 path through cavity 98 indicated. This arrangement, with cavity 98, allows counterweight 80 to have increased volume over designs that would otherwise extend vertical groove 47 through the length of counterweight 80 to accommodate the cable 92. FIG. 30D is a top view of the counterweight shown in FIGS. 30A and 30B. Apertures 56 are shown that couple counterweight 80 to cables 90 according to one embodiment.

It should again be noted that the transport components for boom apparatus 70 can be used whether or not column 30 is of a fixed height or has movable section 34 to allow height variation.

Adjustable Handle Configurations

Another problem related generally to equipment portability and height adjustment is adjustment of drive handle grip 625 height (FIG. 1) for the technician. It is instructive to note that portable radiography devices, although compact, have considerable weight that can be in excess of 1000 pounds, for example. A supporting transport drive system, in response to operator control, allows mobile radiography unit 20 to be moved easily forward and backward and steered without excessive effort from the operator. For this purpose, drive handle grip 625 is operatively connected with various sensors that respond to forces applied against handle grip 625 by the operator and serves to interpret the applied forces for steering and movement of the mobile radiography apparatus.

Figure 31:
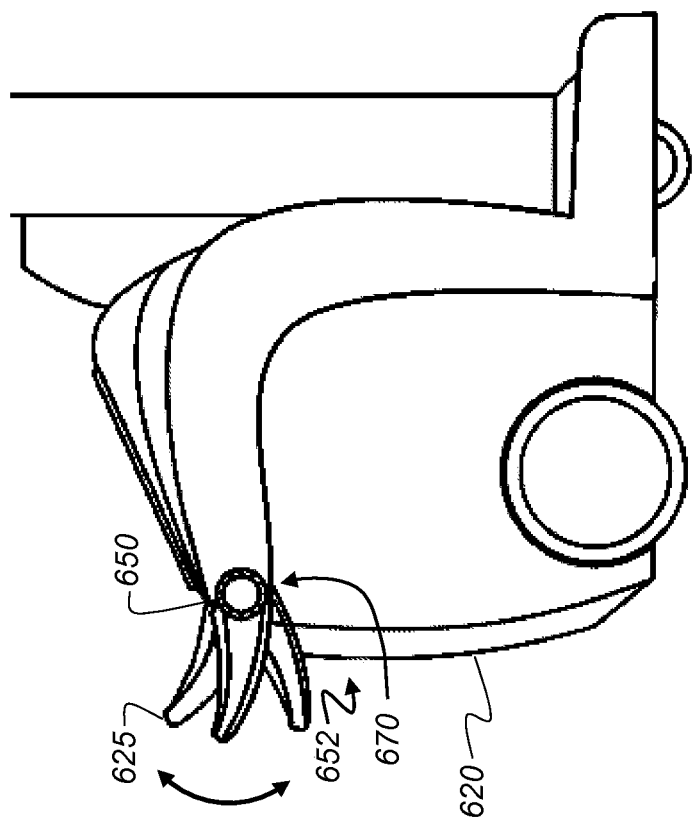
FIG. 31 is a side view of the frame of a portable radiography system showing a handle height adjustment.

An embodiment of the present invention allows technician adjustment of drive handle height, preferably without tools. Straightforward height adjustment can be made in a number of ways, such as by pivoting handle grip 625 as shown in FIG. 31. In this embodiment, the operator loosens a knob 650 at the rear 652 of frame 620, pivots the handle upwards or downwards to an appropriate height, then retightens the knob. It can be appreciated that various other types of detent mechanisms could be used, allowing handle grip 625 to be adjusted by the operator to two or more height positions for controlling a transport drive system 670. Transport drive system 670 includes the set of manual and logic control elements, motors, brake elements, sensors, wheels, and related components for movement and steering of the mobile apparatus. Preferably, operator adjustment is intuitive, so that an operator can perform this adjustment easily and within a short time.

One familiar example of a pivoting mechanism utilizes a circular element with a series of holes that serve as detent locations. This can be combined with a spring biased detent locking pin. The circular element can be the exterior of a cylinder with a series of detent holes in line along the circumference. Alternately, the circular element can take the form of a sheet face with a series of detent holes positioned in a circular pattern. The spring biased detent locking pin can be manually extracted by hand in order to allow the handle to be indexed to the desired rotary position.

Figure 32:
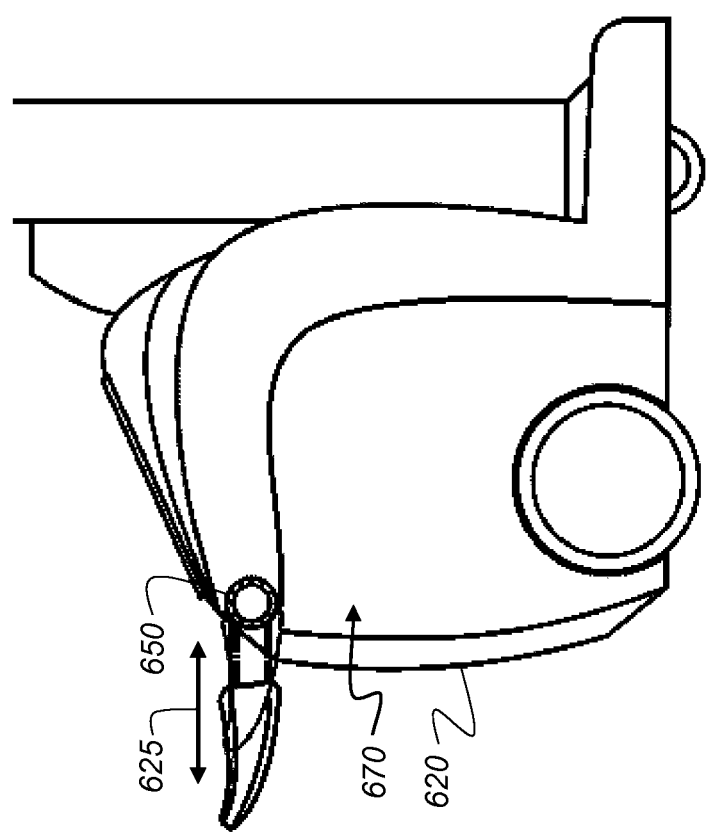
FIG. 32 is a side view of the frame of a portable radiography system showing adjustment of handle extension.

FIG. 32 shows another adjustment for transporting mobile radiography unit 20 more easily, allowing variable horizontal extension of handle grip 625, outward from frame 620. In one embodiment, knob 650 is used for both pivoting as in FIG. 31 and extension as in FIG. 32. It can be appreciated that any of a number of different types of adjustable mechanical linkage can be used for handle grip 625 extension.

FIGS. 33A, 33B, and 34 show an alternate embodiment for transport drive system control in which a separate handle grip 625 on frame 620 is optional, not required. For this embodiment, the operator controls frame 620 movement through transport drive system 670 with boom 70 and its associated tube head 100 in docked position. The operator then uses tube head handles 660 that are on both sides of tube head 100. When the tube head assembly is undocked, handles 660 help position and extend boom assembly 70 horizontally, vertically, and in rotation. When the tube head assembly 100 is docked, as is shown in the front and side views of FIGS. 33A and 33B, respectively, handle 660 can be used for transport drive control. Buttons or other controls 662 mounted on the tube head handles 660 can be used as control elements of transport drive system 670 to drive the cart forwards and backwards at suitable speed, for steering, and to provide slow speed or fine position transport.

Embodiments of the present invention thus incorporate the transport drive handle features directly on the tube head assembly, providing transport drive control from handles 660. This feature can replace or supplement handle grip 625 of FIGS. 31 and 32 as an alternative, according to operator preference. Controls 660 provide throttles and directional sensing for steering when handles 660 are used. Additional controls for transport can be provided, such as control knobs or pistol-grip switches for setting speed and direction. Lockout switching is provided to prevent movement of frame 620 unless boom apparatus 70 is in a docked position.

FIG. 34 shows an additional advantage that is available using handles 660 for transport drive control. The technician transporting frame 620 can dock boom apparatus 70 at a variable height and extension, then use handles 660 for steering and other transport drive control functions. Advantageously, boom adjustment can be made without tools. Methods for handle incremental position adjustment and locking include but are not limited to detent mechanisms.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention.

PARTS LIST

20. Mobile radiography unit
22. Transport frame
30. Sectioned vertical column
32. Base section
34, 36. Movable section
38. Vertical column
40. Boom transport mechanism
42. Track
44. Carriage
46, 47, 48. Groove
50. Plate
52. Brake
54. Wheel
56. Aperture
58. Wheel
60. Block
62. Mobile radiography unit
64. Column
66. Technician
68. X-ray source
70. Boom apparatus
72. Opening
74. Accessory
76. Sleeve
78. Shaft
79. Top edge
80. Counterweight
81. Extended section
82. Pulley
83. Cap
84. Pulley
86. Wheel
88. Motor
90, 92. Cable
96. Shelf
98. Cavity
100. Tube head
600. Mobile radiography unit
610. Display
612. Control panel
615. Wheel
620. Frame
625. Handle grip
635. Support member
640. X-ray source
650. Knob
652. Frame
660. Handle
662. Control
670. Transport drive system
D1, D2. Distance
G. Mechanical ground
H. Horizontal axis
H1. Height
H2. Shaft height
L. Line
L1, L2. Length
S. Force
V. Vertical axis

What is claimed is:

1. A mobile radiography apparatus comprising:
   a portable transport frame;
   a sectioned vertical column mounted on the frame and defining a vertical axis and comprising a base section having a fixed vertical position relative to the vertical axis and at least one movable section that is translatable to a variable vertical position along the vertical axis;
   a boom apparatus that supports an x-ray source and extends outward from the movable section and has an adjustable height relative to the vertical axis for positioning the x-ray source; and
   a counterweight that is operatively coupled to the boom apparatus to support displacement of the boom apparatus to any of a plurality of vertical positions along the movable section, wherein the counterweight, in cooperation with boom apparatus movement, travels along the sectioned vertical column,
   wherein, at one or more of the height positions of the boom apparatus, a portion of the counterweight extends upward above the sectioned vertical column.

2. The apparatus of claim 1 further comprising a plurality of pulleys internal to the column and cooperating to provide simultaneous vertical movement of the boom apparatus and the at least one movable section.

3. The apparatus of claim 1 further comprising a brake mechanism that, when actuated, constrains vertical movement of the at least first movable section.

4. The apparatus of claim 1 wherein the sectioned vertical column is at least partially rotatable about the vertical axis.

5. The apparatus of claim 1 wherein the at least one movable section is at least partially rotatable about the base section.

6. The apparatus of claim 1 further comprising a boom transport mechanism that couples the boom apparatus to the at least one movable section, wherein the boom transport mechanism is actuable to provide vertical movement along at least a portion of the first movable section.

7. The apparatus of claim 1 further comprising one or more pulleys and cables that allow simultaneous vertical and rotational movement of the boom apparatus relative to the vertical axis.

8. The apparatus of claim 1 wherein the counterweight has one or more vertical grooves allowing at least a portion of the counterweight to travel past a pulley.

9. The apparatus of claim 1 wherein the counterweight provides a vertical cavity that allows cable travel inside a portion of the counterweight.

10. The apparatus of claim 1 wherein the height of the portion of the counterweight that extends upward above the sectioned vertical column depends on both the vertical displacement of the boom and the vertical position of the movable section.

11. A mobile radiography apparatus comprising:
a portable transport frame;
a sectioned vertical column mounted on the frame and defining a vertical axis and comprising a base section having a fixed vertical position relative to the vertical axis and at least a first movable section that is translatable to a variable vertical position along the vertical axis;
a boom transport mechanism on the first movable section, wherein the boom transport mechanism is actuable to adjust to a height position by moving along at least a portion of the first movable section;
a boom apparatus that supports an x-ray source and is coupled to the boom transport mechanism and extends outward with respect to the sectioned vertical column; and
a counterweight that is operatively coupled to the boom transport mechanism for displacement to any of a plurality of vertical positions, along a shaft that extends within the first movable section of the vertical column, in cooperation with boom apparatus movement,
wherein the counterweight has a vertical cavity that is disposed to accept a cable that travels inside the counterweight, the cable extending between two or more pulleys that provide movement of the first movable section.

12. The apparatus of claim 11 further comprising a brake mechanism that constrains vertical movement of the first movable section and that actuates automatically when the sectioned vertical column is in a collapsed position.

13. The apparatus of claim 11 wherein the sectioned vertical column further comprises at least one middle section that is between the base section and the first movable section, wherein the at least one middle section is translatable to a variable vertical position along the vertical axis.

14. The apparatus of claim 11 further comprising a motor disposed to provide vertical movement of the first movable section.

15. The apparatus of claim 11 wherein the boom transport mechanism is coupled to the first movable section by a wheeled carriage that is movable within a track.

16. The apparatus of claim 11 wherein the sectioned vertical column is at least partially rotatable about the vertical axis.

17. A method for mounting an x-ray source for use at variable heights, the method comprising:
providing a sectioned vertical column that comprises a base section having a fixed vertical position relative to a vertical axis and at least a first movable section that is translatable to a variable vertical position along the vertical axis;
coupling a boom transport mechanism onto the first movable section, wherein the boom transport mechanism is actuable to provide vertical movement along at least a portion of the first movable section;
coupling a boom apparatus to the boom transport mechanism, the boom transport mechanism having an x-ray source for positioning at a desired height; and
coupling a counterweight to the boom transport mechanism, wherein the counterweight travels in the direction of the vertical axis within a shaft in the first movable section of the vertical column and wherein a portion of the counterweight extends upward above the shaft at one or more positions of the boom transport mechanism.

18. The method of claim 17 further comprising providing a cavity inside the counterweight to allow travel of a connecting cable for supporting vertical translation of the at least the first movable section.

19. The apparatus of claim 1 further comprising:
a transport drive system comprising a drive handle responsive to operator control for movement and steering,
wherein the drive handle is adjustable for at least one of height and extension.

20. The apparatus of claim 1 further comprising:
a transport drive system comprising a drive handle that is mounted on the boom and that is responsive to operator control for movement and steering.

* * * * *